United States Patent
Finlay et al.

(10) Patent No.: US 10,912,472 B2
(45) Date of Patent: Feb. 9, 2021

(54) METHODS AND SYSTEMS USEFUL IN MAPPING HEART RHYTHM ABNORMALITIES

(71) Applicant: BARTS HEALTH NHS TRUST, London (GB)

(72) Inventors: Malcolm Finlay, London (GB); Shohreh Honarbakhsh, London (GB); Richard Schilling, London (GB); Ross Hunter, London (GB); Waqas Ullah, London (GB)

(73) Assignee: BARTS HEALTH NHS TRUST, London (GB)

( * ) Notice: Subject to any disclaimer, the term of this patent is extended or adjusted under 35 U.S.C. 154(b) by 0 days.

(21) Appl. No.: 16/891,661

(22) Filed: Jun. 3, 2020

(65) Prior Publication Data

US 2020/0359924 A1 Nov. 19, 2020

Related U.S. Application Data

(63) Continuation of application No. PCT/EP2019/060367, filed on Apr. 23, 2019.

(30) Foreign Application Priority Data

Apr. 23, 2018 (GB) .................................. 1806580.5

(51) Int. Cl.
*A61B 5/00* (2006.01)
*A61B 5/04* (2006.01)
(Continued)

(52) U.S. Cl.
CPC ...... *A61B 5/04012* (2013.01); *A61B 5/02028* (2013.01); *A61B 5/046* (2013.01);
(Continued)

(58) Field of Classification Search
CPC ... A61B 5/04012; A61B 5/7264; A61B 5/046; A61B 5/743; A61B 5/0432; A61B 5/02028; A61B 5/0408
See application file for complete search history.

(56) References Cited

U.S. PATENT DOCUMENTS

2013/0150740 A1 6/2013 Narayan et al.
2014/0200473 A1 7/2014 Zeng et al.
(Continued)

FOREIGN PATENT DOCUMENTS

EP 3192438 A1 7/2017

OTHER PUBLICATIONS

Hunter RJ, Diab I, Thomas G et al., Validation of a classification system to grade fractionation in atrial fibrillation and correlation with automated detection systems. Europace : European pacing, arrhythmias, and cardiac electrophysiology : journal of the working groups on cardiac pacing, arrhythmias, and cardiac cellular electrophysiology of the European Society of Cardiology 2009;11:1587-96.

(Continued)

*Primary Examiner* — Scott M. Getzow
(74) *Attorney, Agent, or Firm* — Leason Ellis LLP

(57) ABSTRACT

A computer implemented method and system for identifying one or more areas of the heart muscle responsible for supporting or initiating abnormal heart rhythms using electrogram data recorded from a plurality of electrodes obtained from a corresponding series of sensing locations on the heart over a recording time period; the method including the steps of: setting a pre-defined geodesic distance, dividing the recording time period into several analysis time periods, and pairing each sensing location with a plurality of other sensing locations from within the defined geodesic distance, thus forming a plurality of location pairings; for each of the analysis time periods, defining the relative timing of each activation signal for each location within each pairing, determining whether the relative timing of activation signals falls within plausible biological parameters, defining the leading signal of the pair for each electrogram activation within the respective analysis time period; and assigning a (Continued)

series of lead signal scores to each electrogram pairing acquired within each analysis time period based on the proportion of time within the respective analysis time period that each activation signal is leading within each pairing; repeating the analysis at the same location at least once whilst varying the analysis time period; combining each analysis time period for each signal location to provide a statistical measure of the proportion that each signal location tends to lead relative to other locations within the defined geodesic area; and relating lead signal scores from overlapping geodesic areas to provide relative combined lead signal scores; to provide an indication of the relative likelihood that each sensing location is generally preceding other areas and is therefore at or adjacent to a driver area of the abnormal heart rhythm.

21 Claims, 20 Drawing Sheets

(51) Int. Cl.
  *A61B 5/02*    (2006.01)
  *A61B 5/046*   (2006.01)
  *A61B 5/0432*   (2006.01)
  *A61B 5/0408*   (2006.01)

(52) U.S. Cl.
  CPC .......... *A61B 5/0408* (2013.01); *A61B 5/0432* (2013.01); *A61B 5/7264* (2013.01); *A61B 5/743* (2013.01)

(56) References Cited

U.S. PATENT DOCUMENTS

2014/0336518 A1   11/2014   Shuros et al.
2014/0371609 A1   12/2014   Narayan et al.
2014/0371616 A1   12/2014   Narayan et al.

OTHER PUBLICATIONS

Nademanee K, McKenzie J, Kosar E et al., A new approach for catheter ablation of atrial fibrillation: mapping of the electrophysiologic substrate. Journal of the American College of Cardiology 2004;43:2044-53.

Konings KT, Kirchhof CJ, Smeets JR, Wellens HJ, Penn OC, Allessie MA High-density mapping of electrically induced atrial fibrillation in humans. Circulation. Apr. 1994;89(4):1665-80).

METHODS AND SYSTEMS USEFUL IN MAPPING HEART RHYTHM ABNORMALITIES

CROSS-REFERENCE TO RELATED APPLICATIONS

This application is a U.S. Continuation Application under 35 U.S.C. § 111(a) of International Patent Application No. PCT/EP2019/060367, filed Apr. 23, 2019, which claims priority to European Application No. 1806580.5, filed Apr. 23, 2018, which are hereby incorporated by reference in their respective entireties.

FIELD OF THE INVENTION

The present invention relates to a methods and systems useful in mapping heart rhythm abnormalities and in particular provides methods and systems to identify areas of the heart that are statistically likely to be driving abnormal heart rhythms.

BACKGROUND OF THE INVENTION

Atrial fibrillation (AF) is the most common sustained heart rhythm abnormality. Its incidence is increasing partly due to the aging population and it has been referred to as a growing epidemic. AF results in irregular contractions of the heart causing unpleasant symptoms of palpitations and increasing the risk of stroke, heart failure (HF) and death. Percutaneous catheter ablation (CA) is a safe treatment option in symptomatic patients with AF. The success rate of these procedures have improved with time due to the better understanding of AF, development of new techniques and technology, and greater physician experience. However, the success rate of these procedures still only remains between 50 and 70%.

A major reason for the difficulties found in targeting the specific sites responsible for the persistence and maintenance of AF (hereafter referred to as AF drivers) is the irregular and chaotic nature of activation wavefronts in atrial fibrillation. The constant meandering and instability of individual rotational, re-entry or focal activations makes interpretations of activation sequences very complex.

More recently, a number of computational and electro-anatomical methods have been developed allowing electrical data (i.e. electrograms) recorded from within the atria to be presented to the physician in such a way that particular "driver" areas might be recognised. These drivers might also be easier or harder to recognise depending on the relationship between the frequency of the driver and the frequency of activations from non-driver random and chaotic activity. Panoramic mapping techniques attempt to address this issue. Here, multipolar catheters are inserted into the cardiac chamber of interest and the signals from across the chamber are acquired simultaneously. Examples of this include non-contact mapping (Ensite, Abbott Medical; alternatively Acutus Medical), and particular 2D and 3D contact mapping methods (e.g. Cartofinder, Biosense Webster, J&J; Topera, Abbott Medical; Rhythmia, Boston Scientific). US 2014/0371609 describes an example of one such approach to identifying sources of rhythm disorders.

Known in the art are methods that seek to identify areas of atrial activation that occur prior to activations of neighbouring sensors. One example is exemplified in patent application EP 3 192 438 A1. Here, the inventors propose classifying the proportion of time that an activation precedes its neighbouring sensors and displaying this on a computer-generated representation of the heart chamber. These activations can thereafter be classified and annotated, and a display of the number of times a sensor is activated prior to its neighbouring sensors be displayed dependent on the classification. This method therefore proposes a classification based on neighbouring activations to sensors only, and in many computer and theoretical models of atrial fibrillation (which are based on essentially 2-dimensional representations) such a technique would initially appear sufficient in highlighting areas of key focal activation. However, in the clinical art, conduction can be discontinuous and may be circuitous and truly chaotic within the 3-dimensional wall thickness of the human atrium. Thus comparison with neighbours alone is highly likely to be misleading, for example an aliasing effect may take place whereby an area appears to precede its neighbouring electrodes, but in truth is following through very delayed conduction, or represents far-field activation. This can lead to ablation being performed in incorrect areas, increasing the risk to the patient and prolonging the invasive procedure.

SUMMARY OF THE INVENTION

According to a first aspect of the present invention, there is provided A computer implemented method to identify one or more areas of the heart muscle responsible for supporting or initiating abnormal heart rhythms using electrogram data recorded from a plurality of electrodes obtained from a corresponding series of sensing locations on the heart over a recording time period; the method including the steps of:
setting a pre-defined geodesic distance,
dividing the recording time period into several analysis time periods, and pairing each sensing location with a plurality of other sensing locations from within the defined geodesic distance, thus forming a plurality of location pairings; for each of the analysis time periods, defining the relative timing of each activation signal for each location within each pairing,
determining whether the relative timing of activation signals falls within plausible biological parameters,
defining the leading signal of the pair for each electrogram activation within the respective analysis time period; and
assigning a series of lead signal scores to each electrogram pairing acquired within each analysis time period based on the proportion of time within the respective analysis time period that each activation signal is leading within each pairing;
repeating the analysis at the same location at least once whilst varying the analysis time period;
combining each analysis time period for each signal location to provide a statistical measure of the proportion that each signal location tends to lead relative to other locations within the defined geodesic area; and
relating lead signal scores from overlapping geodesic areas to provide relative combined lead signal scores; to provide an indication of the relative likelihood that each sensing location is generally preceding other areas and is therefore at, or adjacent to a driver area of the abnormal heart rhythm.

The present inventors recognise that slowing and termination of atrial fibrillation (AF) most often occurs when ablation is performed at sites from which activation emanates. One method of determining these sites is to consistently move a multipolar catheter within the heart chamber in the direction of the activation sequence, moving towards the electrode pole that appears to be predominantly "earliest" (noting that activation sequence is not repetitious in AF but varies so a lesser or greater degree over time and between patients). After the catheter is moved beyond a certain point, activation starts getting "later" and further movement in the 2D plane can be performed to determine if a single area is truly consistently a source of activations. Ablation performed at such sites appears to be the most efficacious at slowing or terminating AF. This procedure is greatly complicated by the irregularity and frequently changing activation patterns in AF and the volume of data the operator is able to assimilate at any one time. The more electrogram data available to the operator the more accurate the result of the analysis and mapping, but the more difficult it is to analyse the data. Thus the operator often has to continually be aware of the relative timings and pattern of electrogram activations and how this changes over time. Most methods for solving this problem seek to apply predetermined theories of AF mechanism to relatively low-resolution data and applying various filters to the data in order to try and resolve these mechanisms.

The present inventors recognise that undesirable effects, such as those described above in relation to EP 3 192 438 A1, may be distinguished by an expert by careful analysis of cycle length changes, where an abrupt change in cycle length is propagated through to later-activating sites. Nonetheless, the highly disorganised conduction wavefronts existing in atrial fibrillation frequently exist on the boundaries of effective conduction, that is a minor change in cycle length may result in either conduction slowing (decrementation) at a distant site or failure of conduction, leading to short-circuiting at another and ultimately paradoxical changes in activation timings. Examination and analysis of further aspects of the electrogram signals have been found to enable correct classification of a given sensor as "leading" or "following".

In terms of the plausible biological parameters referred to above, it is well recognised that myocardial cells have a limited range of repolarisation times, i.e the time it takes for a cardiac cell to repolarise and be excitable after depolarisation. It is also well recognised that the conduction velocity of an electrical activation across the myocardium is limited by a minimum previously recorded and plausible velocity and that this may vary depending on the myocardial tissue studied. For example atrial tissue will have a slower conduction velocity than the purkinje tissue within the ventricles. These has been previously studied and defined and can thus be used to create filters because repeated activations at a single site that exceed the parameters previously described in the literature, cannot be activation of the same site, rather local activation and far-field activation recorded on the same electrode or a sequence of activations from one recording electrode to the next. Activations that occur within 70 ms of one another at the same site are considered biologically implausible (See for example, Hunter R J, Diab I, Thomas G et al. Validation of a classification system to grade fractionation in atrial fibrillation and correlation with automated detection systems. Europace: European pacing, arrhythmias, and cardiac electrophysiology: journal of the working groups on cardiac pacing, arrhythmias, and cardiac cellular electrophysiology of the European Society of Cardiology 2009; 11:1587-96; and Nademanee K, McKenzie J, Kosar E et al. A new approach for catheter ablation of atrial fibrillation: mapping of the electrophysiologic substrate. Journal of the American College of Cardiology 2004; 43:2044-53.). Similarly conduction velocities of 54 cm/s have been described human AF and conduction velocities of >60 cm/s may be therefore considered biologically implausible (See for example Konings K T, Kirchhof C J, Smeets J R, Wellens H J, Penn O C, Allessie M A High-density mapping of electrically induced atrial fibrillation in humans. Circulation. 1994 April; 89 (4):1665-80).

Optional features of the invention will now be set out. These are applicable singly or in any combination with any aspect of the invention.

In one or more embodiments, the lead signal scores may be acquired over multiple time periods and are used to identify one or more activation sequences across all the electrodes recorded simultaneously over those time periods.

Activation sequences may be related from overlapping geodesic areas to provide global activation sequences. Electrogram sequences may be grouped based on overall activation sequences and patterns, and electrogram sequences from each of these groups is analysed separately.

A comparison may be made of non-parametric activation sequences over wider groups of sensors. A defined geodesic distance within which activations pairings should be compared allows potentially misleading neighbouring classifications to be identified and aliasing effects rejected. Filtering of signals may also further improve signal identification; this may be of classical signal analysis type, but alternatively may be determined by physiologically plausible parameters. For instance, conduction velocities may be either pre-calculated or calculated from signals directly, if two activation signals fall outside bounds of plausible conduction they may be considered to not be directly related to the same wavefront and therefore the pairing of their signals rejected from analysis.

Another method to avoid aliasing of signals involves assessing the sequence of activation of each pair of sensors multiple times within each analysis time period. In a stepwise manner, for each signal, every potential activation signal is identified. Thereafter, one by one, these activations signals are therefore compared to each activation occurring in all the other sensors within the selected geodesic distance. For each sensor, a comparison is thus made for every activation of that sensor with all of its paired sensors. Multiple arrays of stochastic data are created, one for each sensor, whereby the number of times of that sensor leads its paired sensors within the geodesic distance is easily calculated. The proportion of time that a sensor is leading can therefore be calculated in a straightforward manner.

A key advantage of this method is that sensors which exhibit less frequent activation will contribute to fewer activation pairings. Thus even if such a sensor might erroneously appear to frequently lead their neighbouring sensors, the lower number of activations will reduce the number of times they are calculated to lead, and thus the proportion over a period of time will be lower. A consequence of this method is that bystander circuits that do not critically contribute to the arrhythmia perpetuation will be assigned lower leading scores.

In one or more embodiments, the global signal scores are adjusted based on models of likely relative importance of each signal and location.

In some embodiments, the recording time period is between 5 seconds and 5 minutes.

In some embodiments, the electrogram data additionally comprises spatial data associated with each electrogram signal that identifies the position of the sensing location from which the electrogram signal has been obtained relative to a spatial reference frame.

In such embodiments, the spatial reference frame comprises coordinates for vertices and polygons making up a geometry of a model representing the heart muscle.

In some embodiments, the predefined geodesic distance is no less than 0.2 cm and no more than 6 cm.

In some embodiments, the geodesic distance may be adjusted based on combining signal frequency analysis and calculated or pre-determined conduction velocities.

In some embodiments, the sensing locations are associated with a heart chamber and each sensing location is paired only with other sensing locations that are on the same aspect of the heart chamber.

In some embodiments, the computer implemented method further comprises the step of prioritising or rejecting lead signal scores based on properties of the simultaneously acquired electrograms from the plurality of locations available, the properties including one or more of: cycle length, activation sequence, timings after change in cycle length, and electrogram morphology.

In this way, leading electrograms that are also leading in cycle length change, activation sequence and morphology change may be prioritised; and those that are not may be rejected.

In some embodiments, the combined lead signal scores are modified depending on anatomical location, or other known modifiers acquired during the case or from prior data that are associated with ablation efficacy to provide modified leading signal scores In this way, the combined lead signal scores more accurately reflect the likelihood of ablation in these sites being associated with arrhythmia modification, termination or elimination. Combined lead scores may be normalised.

In some embodiments, modifiers may be generated using one or more of: previous patient data; static or dynamic calculations from raw data; a computational or statistical model.

In some embodiments, the modifiers may be generated using a feedback deep-learning model within a neural network.

In some embodiments, modifiers of the normalised, combined lead signal scores are determined dynamically with respect to cycle length variation as ablation is performed, or from reference to previously acquired cycle length variation during ablation on similar patients, or by reference to previously known patient outcomes from ablation on similar patients, any of which may be statically or dynamically calculated from raw data or from a computational or statistical model.

In some embodiments, it is possible to correctly identify prematurely activating areas and/or areas that conversely are consistently activating later than others, i.e. have low leading signal scores. These late-activating scores may be classified as passively activating and are unlikely to be critical in the perpetuation or generation of arrhythmia. They may therefore be avoided during an ablation procedure. Furthermore, areas of heart chamber bounded by non-conducting structures, for example heart valves or scar, and areas which are consistently seen to have low leading scores can be inferred to be passively activating themselves. By labelling these areas as such they may be safely ignored and attention focussed elsewhere. This may be expected to reduce the time taken during an ablation procedure, mapping and ablation on these areas will be reduced and avoided therefore reducing procedure time and increasing procedure safety.

In some embodiments, the patients own data, such as heart scar distribution, location or size, chamber size and morphology may be used to modify and improve a statistical model, which then is used to further adjust modifiers of the normalised, combined lead signal scores.

In some embodiments, electrograms and locations are dynamically acquired and statistical models are adjusted in real time, whilst at least one sensing location remains predominantly static and zero, one or more sensing location is adjusted in location across the surfaces of heart muscle of interest.

In some embodiments, relative combined lead signal scores are modified dynamically with respect to electrogram data acquired from one or more roaming electrode pairs, or by reference to far-field electrograms or electrocardiogram signals such as surface p-waves.

In some embodiments, activation timings of electrograms from a roaming electrode can be compared to virtual activation timings of nearby locations of previously acquired electrode pairs at specific locations within a geodesic distance by relating to group classifications determined from sensing at other electrode locations.

In some embodiments, resulting signal scores and treatment information are coupled to procedural or clinical outcome data, and is used as a training dataset of a deep-learning model within a neural network.

Clinical outcome data may include medical notes, clinical outcome databases, patient reported outcome measures, ECG data, telemetry data, data from wearable or implantable devices, patient activity monitors or any other physiological measuring tool.

In some embodiments, procedural outcome data may be cycle lengths, heart rhythm, electrode activation sequences.

In some embodiments, procedural factors such as location of ablation, time of ablation, and energy of ablation are used as inputs to the model.

In some embodiments, areas of the heart generally bounded by late activating areas, or non-conducting anatomical areas are highlighted as areas which are therefore not critical in the maintenance or initiation of arrhythmia.

In some embodiments, areas bounded by areas identified as being non-critical to arrhythmia maintenance or initiation are indicated as areas where treatment is less likely to be necessary for effective treatment of arrhythmia.

In some embodiments, the method further comprising generating a display output to display a graphical representation of the assigned lead signal scores, wherein the graphical representation is a 3D graphical representation with graphical representations of the lead signal scores displayed in spatial arrangement corresponding to the spatial arrangement of the corresponding sensing locations on the heart.

In some embodiments, the graphical representations of lead signal scores are overlaid on a 3D graphical representation of the heart.

In some embodiments, a colour scale is used to represent the relative values of the lead signal scores.

In some embodiments, graphical representations of the lead signal scores vary in size with graphical representations of higher lead signal scores being large in size than those for lower lead value scores.

In some embodiments, the method further comprises the step of acquiring the electrogram data. In such embodiments, the electrogram data may be obtained for the whole recording time period before the data is subsequently processed to calculate the lead signal scores.

In some embodiments, the cardiac electrogram data is obtained from non-contact mapping data from cardiac catheters or from surface ECG electrodes.

According to a second aspect of the present invention, there is provided a computer system for identifying one or more areas of the heart muscle responsible for supporting or initiating abnormal heart rhythms using electrogram data recorded from a plurality of electrodes obtained from a corresponding series of sensing locations on the heart, the system comprising:
   a processor;
   a first memory for storing received electrogram data; and
   a second memory having program code stored therein that when executed by the processor causes the system to:
      set or allow a pre-defined geodesic distance to be set,
      divide the recording time period into several analysis time periods, pairing each sensing location with a plurality of other sensing locations from within the defined geodesic distance, thus forming a plurality of location pairings;
      for each of the analysis time periods, define the relative timing of each activation signal for each location within each pairing,
      determine whether the relative timing of activation signals falls within plausible biological parameters,
      define the leading signal of the pair for each electrogram activation within the respective analysis time period; and
      assign a series of lead signal scores to each electrogram pairing acquired within each analysis time period based on the proportion of time within the respective analysis time period that each activation signal is leading within each pairing;
      repeat the analysis at the same location at least once whilst varying the analysis time period; and
      combine each analysis time period for each signal location to provide a statistical measure of the proportion that each signal location tends to lead relative to other locations within the defined geodesic area;
      relate lead signal scores from overlapping geodesic areas to provide relative combined lead signal scores;
      provide an indication of the relative likelihood that each sensing location is generally preceding other areas and is therefore at or adjacent to a driver area of the abnormal heart rhythm.

The second memory may be the same or a different physical memory from the first memory.

Each of the optional features described above in relation to the first aspect (i.e. the computer implemented method) may equally be applied to the second aspect (i.e. the computer system) or the third aspect of the present invention.

According to a third aspect of the present invention, there is provided a computer program comprising instructions which, when the program is executed by a computer, cause the computer to carry out the method of any one of claims 1 to 9.

Further optional features of the invention are set out below.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

In the embodiments described below, the system may be used in conjunction with whole-chamber basket catheters (Constellation catheter, Boston Scientific, ltd, US and FIR-Map catheter, Abbott, US) to allow for simultaneous panoramic left atrium (LA) mapping. However, other suitable catheters/electrodes may be used for obtaining electrogram data and it is not necessary to collect data from the whole area of interest simultaneously. The area of interest can, for example, be divided into smaller areas, electrogram data collected and analysed for each smaller area. The results of the analysis may then being combined and displayed in a single STAR map.

Figure 1:
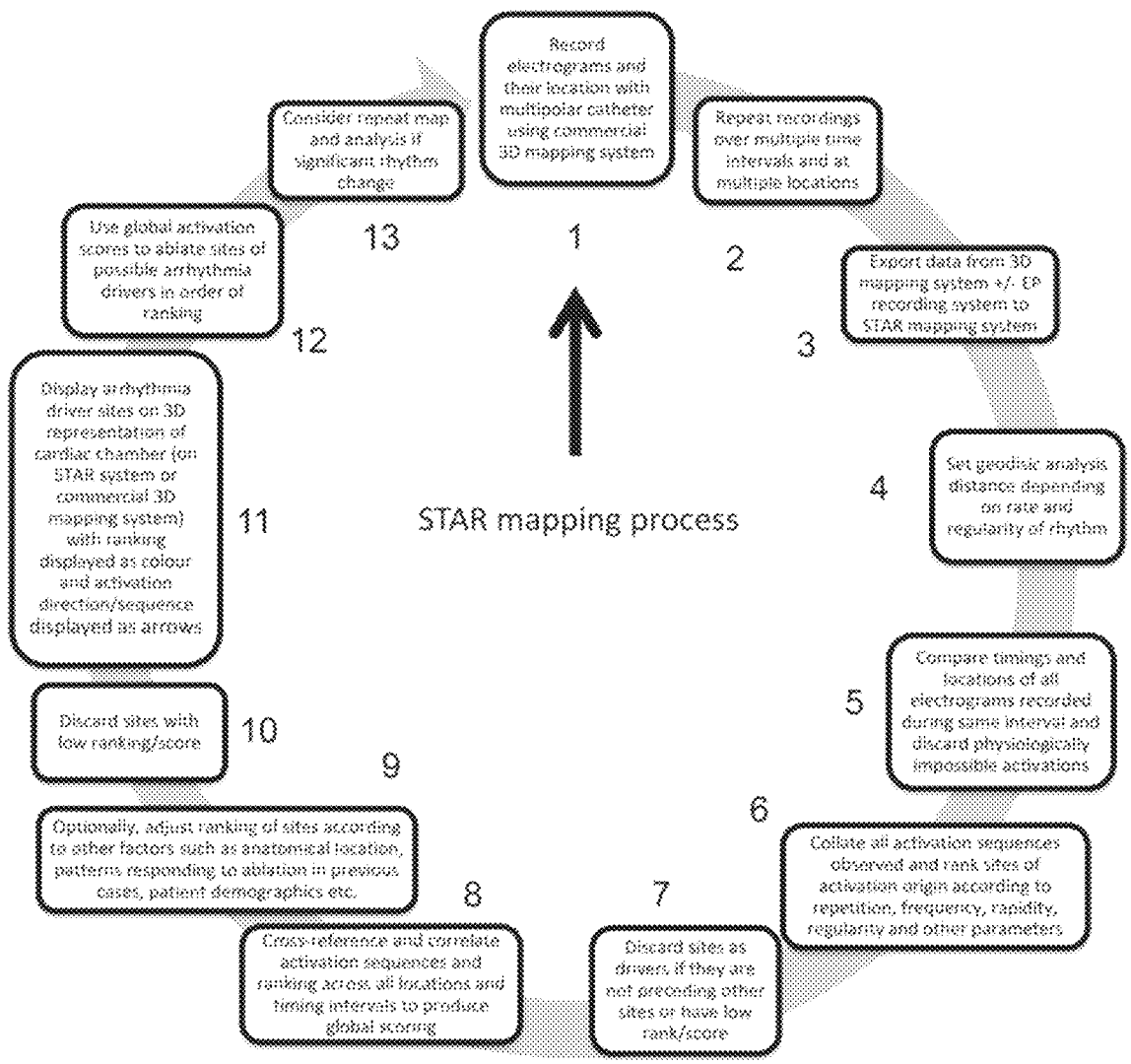
FIG. 1 shows a flow diagram of an embodiment of a method according to the present invention, which may be referred to as the STAR mapping process.

The embodiments below disclose a mapping system, referred to in the following as the "stochastic trajectory analysis of ranked signals (STAR) mapping" system, and developed with the aim to identify sites of drivers of cardiac arrhythmias, which can for example be displayed in the form of a 3D map. Maps created using the STAR-mapping system are referred to in the following as "STAR maps". A detailed example of such a STAR mapping process is shown in FIG. 1.

When carrying out the method, a physician may place a multipolar panoramic mapping catheter in the lateral left atrium, acquire data for a period of time (e.g. 5 seconds to 5 minutes), then reposition the catheter to ensure close apposition to the left atrial septum or anterior wall and another recording performed.

Figure 10:
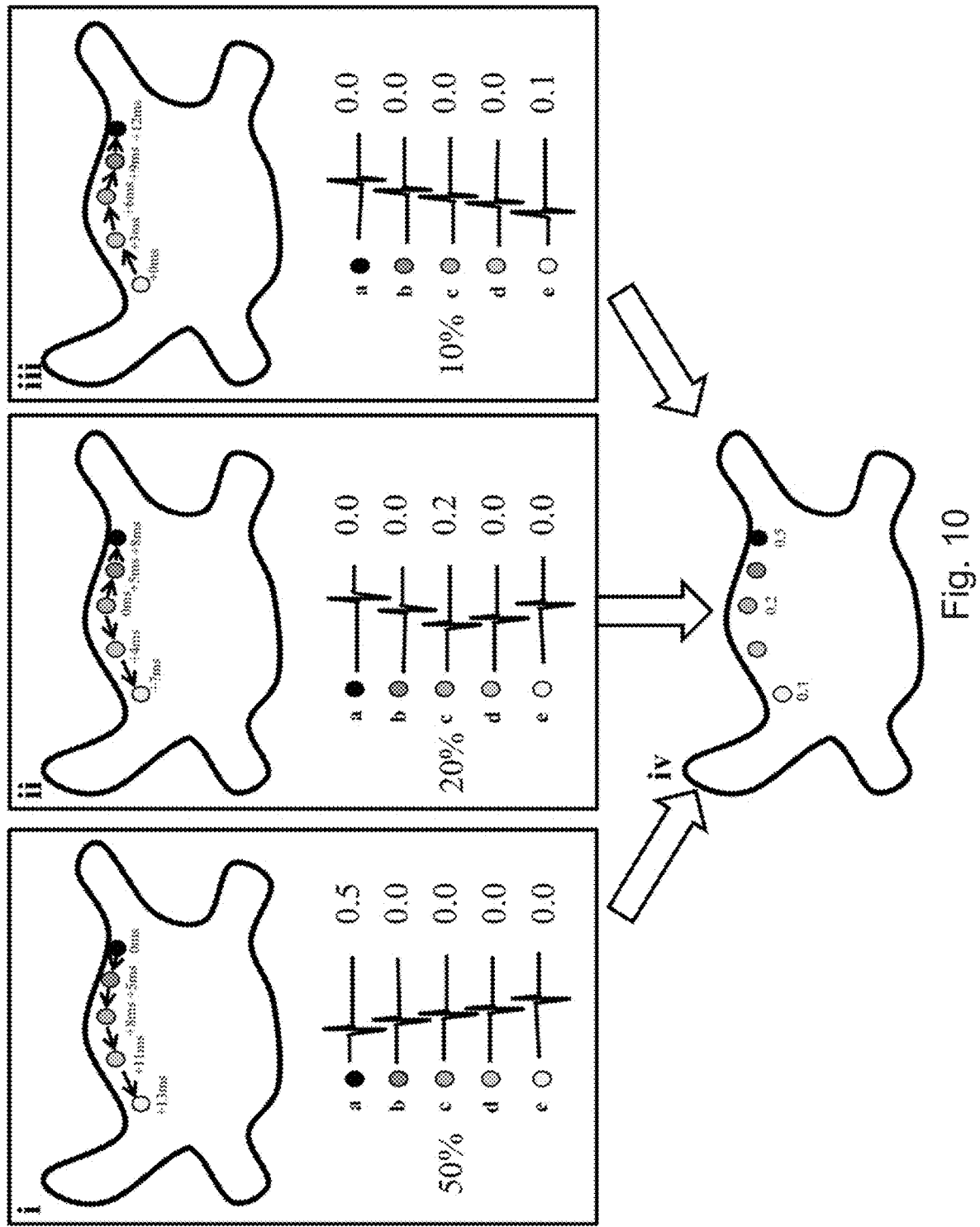
FIG. 10 depicts a schematic diagram of a simplified process of calculating a map.
Figure 11A:
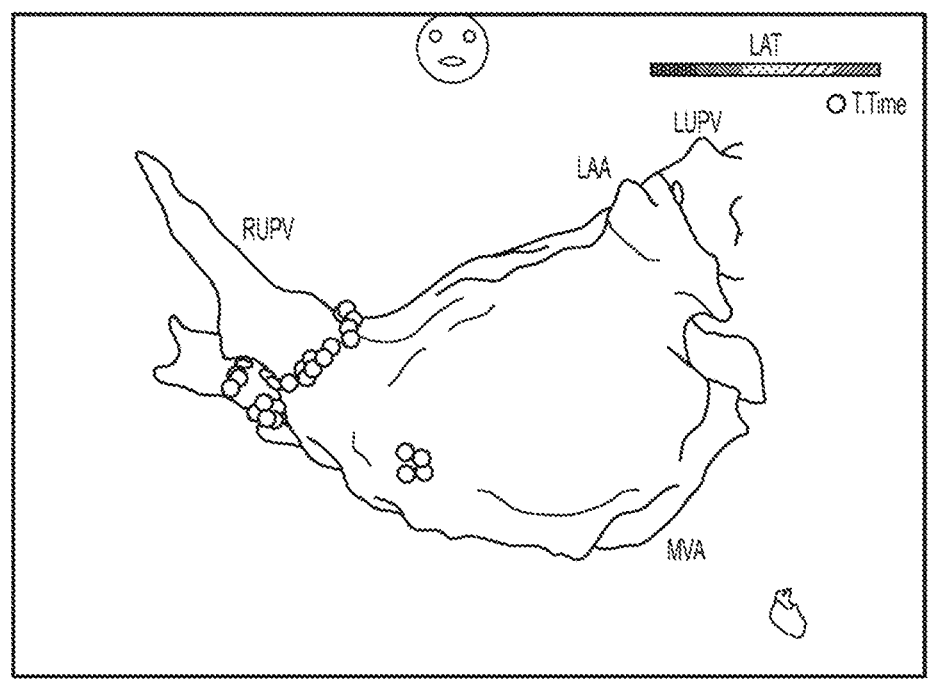
FIGS. 11A and 11B show further examples of 3D maps produced using a method according to an embodiment of the present invention along with corresponding local activation timing maps.
Figure 11B:
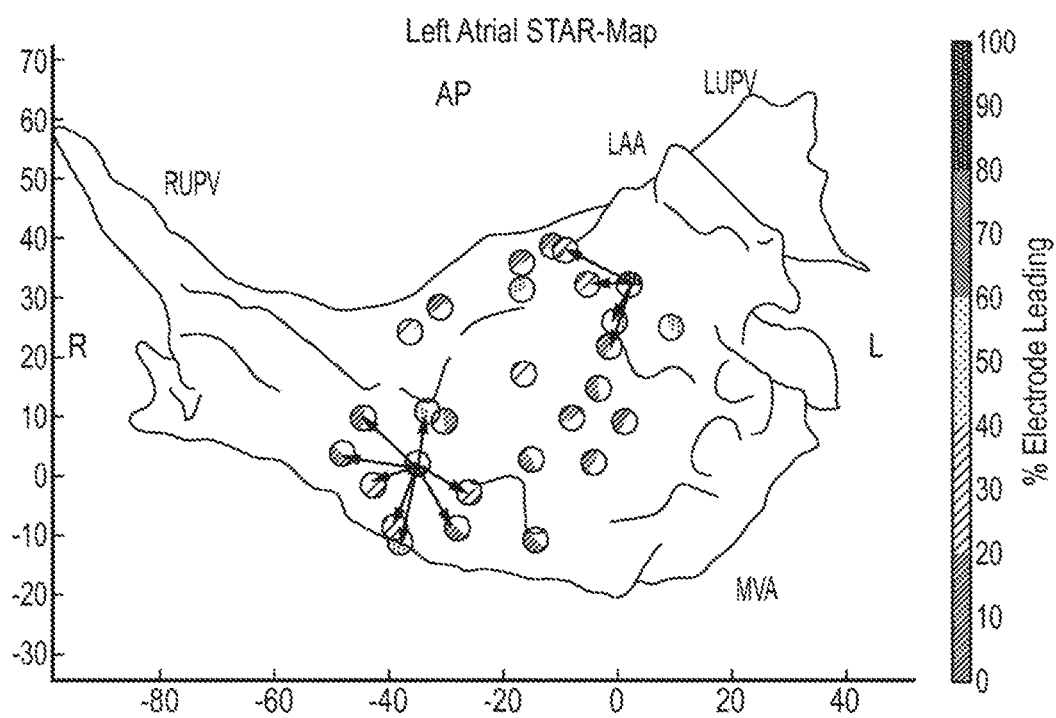
Figure 11C:
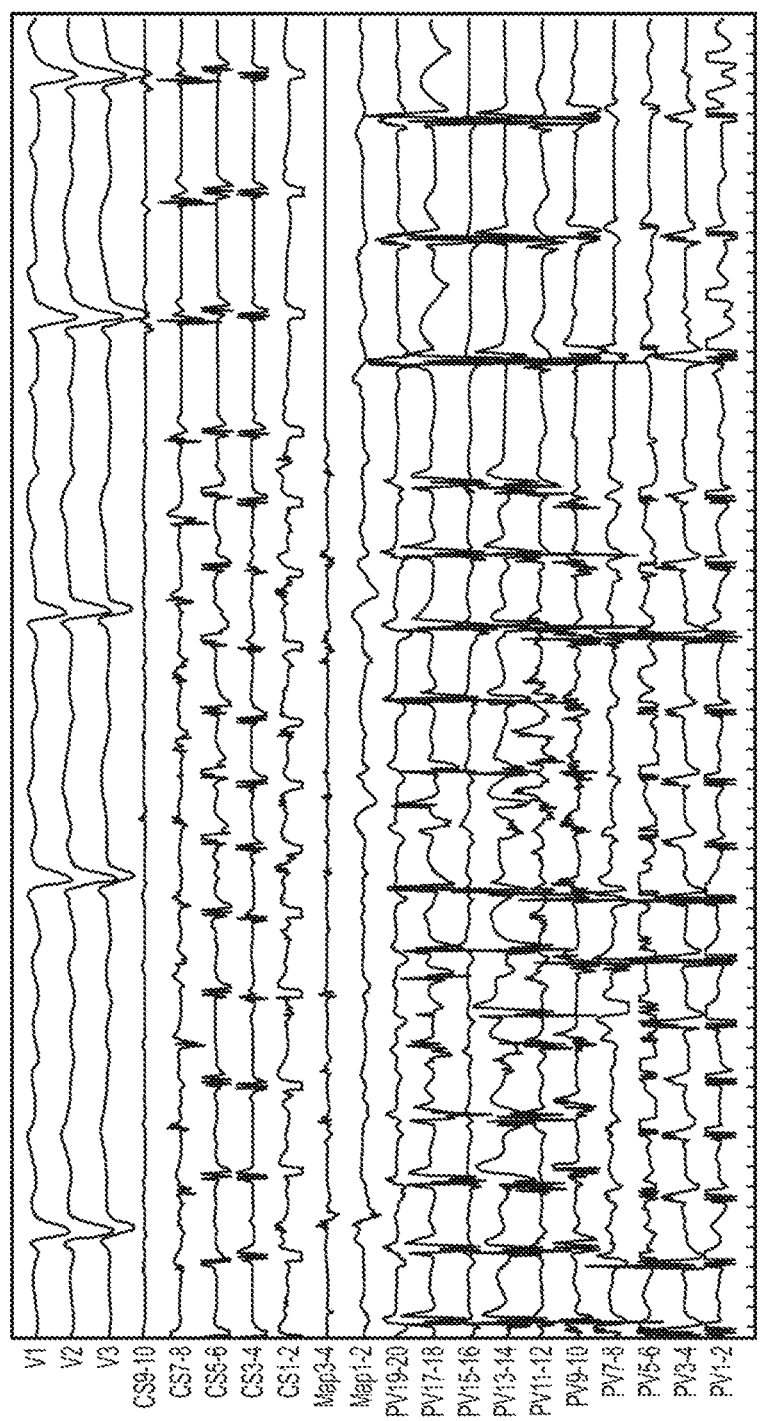
FIG. 11C depicts corresponding electrograms with the impact of ablation at the leading sites shown as organisation of the rhythm.

FIGS. 6 and 10 depicts a simplified schematic diagram of a method of calculating a map. Proportions of "leading" electrode will be coherent between maps, therefore data and proportions would be able to be displayed on the same map without problem. In this way, multiple coherent statistical maps may be built up sequentially by moving catheters within the chamber and taking further recordings.

A principle of the system is to identify sites that generate activations that contribute mechanistically to the maintenance of cardiac arrhythmia, of which AF is the commonest. Due to the chaotic nature of AF and the variability of AF cycle length (CL) it is not feasible to determine sites of earliest activation in relation to a fixed reference point.

The system used to obtain and process the electrogram data typically includes one or more multipolar electrical catheters (e.g. the basket catheters referred to above) which are inserted into a cardiac chamber of a patient, an amplifier and analogue to digital (AD) converter, a console including a signal analyser, processor and GPU, display unit, control computer unit, system for determining and integrating 3D positional information of electrodes.

The system may use known hardware and software such as the Carto™ system (Biosense Webster, J&J), NavX Precision™ (Abbott Medical) or Rhythmia™ (Boston Scientific) for catheters, 3D electroanatomical integration and processing units. Catheters such as "basket" catheters, circular or multi-spline mapping catheters (e.g. Lasso catheter, Biosense Webster, J&J, HD-mapping catheter, Abbott Medical SJM, Pentarray Biosense Webster, J&J), decapolar catheters or ablation catheters may be used. These systems and catheters are used to gather electrogram signals and corresponding location and time data pertaining to electrical activity at different locations within the heart chamber. These data are passed to a processing unit which performs algorithmic calculations on these data and aims to translate these data to provide location information to the physician on the areas within the heart which are most likely to be responsible for the maintenance and persistence of abnormal heart rhythms. Alternatively, the system may use bespoke catheters, tracking systems, signal amplifiers, control units, computation systems and displays.

The STAR-mapping algorithm has been validated ex-vivo using multi-electrode arrays and optical mapping to simultaneously map electrical activity and calcium transit in HL1 cells (immortal murine cardiac cells). It has also been validated in patients with i) atrial paced beats in sinus rhythm and ii) atrial tachycardia (AT) where the mechanism was confirmed with conventional mapping, entrainment and response to ablation.

Before considering the STAR mapping approach in more detail, it is useful to provide an overview of the main steps in the process that is used to identify "leading" signals (that are indicative of areas/sites in the heart that are statistically likely to be driving abnormal heart rhythms), following acquisition of the electrogram data (along with corresponding spatial and temporal data).

First, interference and far-field signal components are removed from input electrogram signals. In one embodiment, the system breaks down signals into relevant components e.g. by spectral analysis, far-field signal blanking, far-field signal subtraction, filtering or by another method known in the art. Signal components originating within the chamber of interest in the heart (e.g. atrial signals) are identified. Relative timings of atrial signals are established, which may be in an explicit, stochastic or probabilistic manner. In some embodiments, the phase of each signal may be determined and relative timings established from relative phase shifts between different electrodes.

Second, signal timings from adjacent electrodes are paired. Signals are only paired with one another if electrode locations are within a specified geodesic distance from one another i.e. only electrodes close to each other are paired to each other. This may be further improved by only pairing electrodes that are located on the same aspect of the chamber wall; i.e. adjacent electrodes on the back wall of the heart will be considered adjacent but not if the electrodes are on opposite sides of a discontinuity, e.g. a pulmonary vein, even though the absolute distance between such electrodes may be small. Relative timings of activation at paired electrodes is thus established, with a value to a "leading" electrode ascribed. This pairing may be carried out for discrete analysis time periods, typically of between 10 ms and 200 ms in duration. The length of the analysis time periods need not be constant across all of the data being analysed. The aim is to compare timings between activation of paired electrodes caused by the same activation sequence and the analysis time periods can be determined accordingly. For example, each analysis time period can be chosen to encompass electrode activations that are likely to have resulted from the same activation sequence. Accordingly, analysis time periods may overlap one another.

Third, this process is repeated many times (i.e. for many analysis time periods, for each pairing) over a given period of time. Advantageously, the analysis time period overlaps, and is shifted in relation to the initial analysis time period for example 10 to 120 seconds. Within the given period of time, the analysis time periods may overlap, as noted above. For example, if the analysis time period is 200 ms, the analysis time periods may overlap by 100 ms, i.e. 50%. In other words, the leading electrodes are determined for a first 200 ms period, then for a second 200 ms time period, the second time period starting 100 ms after the start of the first time period, and so on, for the given period of time. As with the analysis time periods themselves, the degree of overlap may vary over the data set. By such repetitive analysis it is possible to discard activation sequences that repeat less frequently or not at all and rank activations sequences that appear more frequently with more importance and priority.

In atrial fibrillation the activation patterns appear chaotic with frequent changes in wavefront propagation. The relative proportions of 'time' that each site precedes each of its neighbors in the activations mapped is calculated, and thus a proportional map of the more frequently "leading" electrode sites is created.

Fourth, proportions of 'time' that each recorded area spends "leading" activations are calculated. This calculation may be based on actual duration of time during which each electrode is judged to be leading its paired electrodes. Alternatively, it may be the proportion of total analysis time periods (whether those time periods are of the same or different durations to one another) for which the site leads in mapped activations. Thus, in some examples, the relative proportions are in effect determined by looking at the total number of atrial activation signals seen by a given electrode and determining the proportion of those activation signals for which the electrode is leading relative to a plurality of other electrodes paired with one another. Although mapping only adjacent electrodes may give rise to errors, the system maps all electrodes relative to all others for each cycle of activation to establish within the mapped field the direction of activation. Sequences are analysed to identify dominant activation sequence during the recording period and the sites that are leading those activations, i.e. the point from which the activations emanate. Activation sequences with a trajectory suggesting a localised source are presumed to be mechanistically important. The STAR mapping system therefore calculates the proportion of activation sequences with a given vector to establish the dominant vector (if any) and the proportion of the time that activations follow that vector. For all sites within the mapping field the proportion of mapped activations originating from that site is calculated to determine its relative importance.

The calculated proportion is normalised so that proportions may be compared across the heart. Many embodiments of the statistical processes, normalisation and subsequent display of this data can be envisaged.

Electrodes which are overlying completely passive areas of cardiac activation will tend towards having few if any activations appearing to emanate from these. Only activation sites that tend to be frequently "leading" within activation sequences will be ascribed values indicating a high likelihood of being a source of activation. Similarly when considering overlapping electrode sampling locations A and B with activation repeatedly earliest at the edge of the sample A, activation may be seen progressing from B to A and thus the sites of early activation of A may be regarded as passive and electrodes from sample B being regarded as leading, thus greater emphasis be given to leading electrodes from sample B. This process may be repeated over multiple recording time periods and locations in order to further refine and define patterns of activation that repeat and discard those that do not, thus building up a wider area of mapping than might be achieved from a single activation recording from a multipolar electrode catheter.

Fifth, a graphical representation of the calculated metrics is displayed on a display unit. In one preferential embodiment, a highlighted point is indicated over the most frequent leading electrodes. Another preferential embodiment includes the assignment of a colour scale to represent the proportion of time an electrode is "leading" activation sequences. This colour scale may be presented on points or on a geometrical shell or other anatomical representation of the chamber of interest. Such a colour scale may be linear, binary, stepwise or non-linear in a manner of ways known in the art. Interpolation of varying descriptions may be used to allow inference to be made across areas without dense electrode coverage. Given a priori knowledge of the data scale, the physician can target the areas in the vicinity of "leading" areas within the chamber of interest for ablation or other treatment. Conveniently, the colour scale (or other graphical representations of the calculated metrics) can be displayed using a projection of the metrics onto the same anatomical geometry as will be used during the ablation procedure.

In some embodiments, the system to highlight areas bounded by passively activating areas. Treating such areas are unlikely to benefit the patient or terminate an arrhythmia, thus by highlighting these passively activating areas excess treatment may be avoided and procedural risks reduced.

A further embodiment of this system may use electrogram or signal timing derived from a non-contact or non-invasive mapping system, with numbers of virtual electrodes which may be effectively unlimited other than by the spatial resolution of the calculated non-contact maps acquired.

Various aspects of the STAR mapping system are discussed in more detail below.

i) Pole Pairing and Geodesic Distance

One potential difficulty with mapping of cardiac electrical activation sequence is that poles that are near to each other, yet are in contact with surfaces that are some distance apart (e.g. poles anteriorly paired with poles posteriorly) can give inaccurate results. As these poles are mapping different aspects of the anatomical geometry they will not be seeing the same wavefront and as a result the activations times obtained would be inaccurate. To overcome this, poles are only paired if they are within a pre-defined geodesic distance from each other. This is determined through taking the projected pole position on the geometry and calculating the distance between the projected poles as if you were travelling on the surface of the geometry i.e. geodesic distance.

Figure 2A:
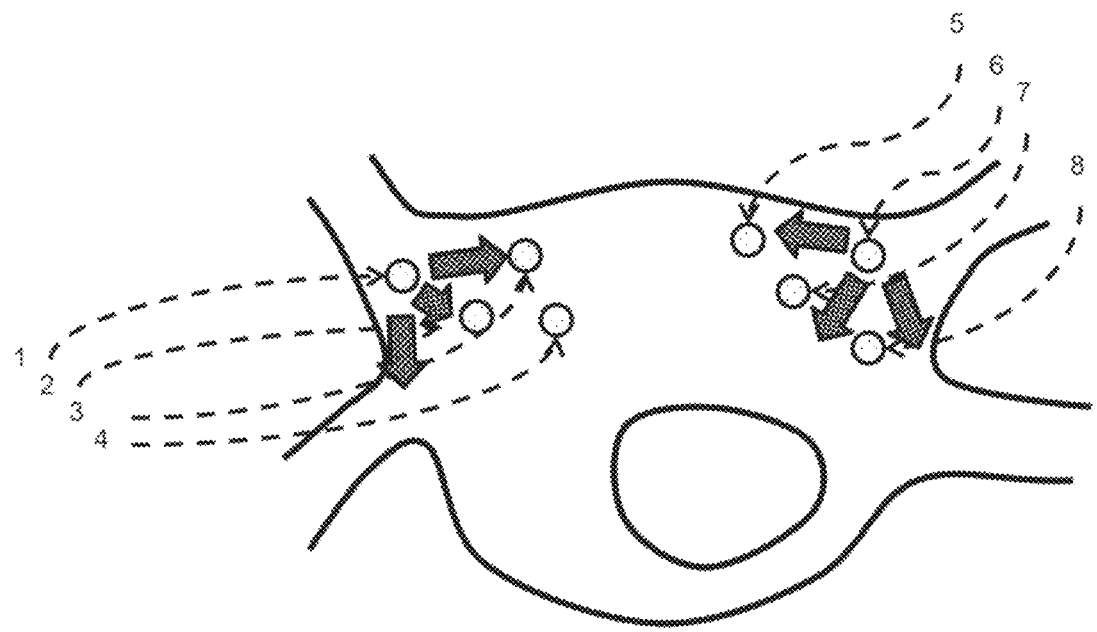
FIGS. 2A-2E depicts an example of electrodes placed at various locations around the heart and the importance of geodesic distance on the analysis of resulting signals.

The effects of geodesic distance can be better understood with reference to FIGS. 2A-2E. Consider a series of electrode locations placed around the left atrium. FIG. 2A shows the electrode positions and a ground truth of the wavefront directions, in this example emanating roughly from electrodes 1 and electrode 7, shown by the thick shaded arrows. In AF this would be expected with multiple areas emitting wavefronts, the proportion of which they emerge from such areas varying over time.

Figure 2B:
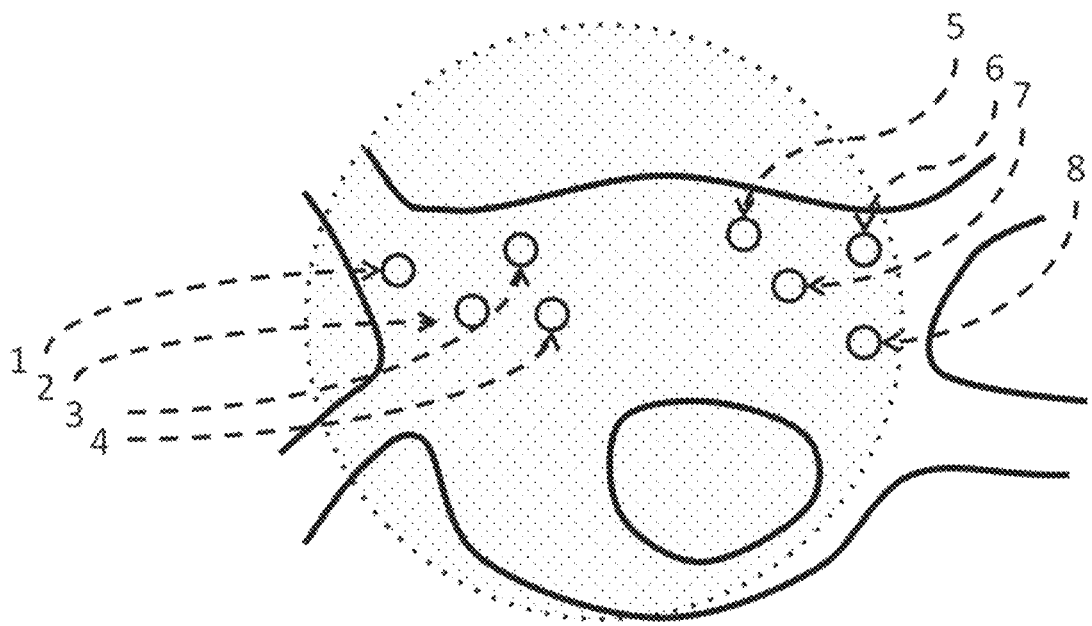

FIG. 2B shows an example of the situation whereby a large geodistic distance is applied in this case, here considering the case of electrode 4. Electrode 4 now will be compared with wavefronts activating electrodes 6 and 8.

Figure 2C:
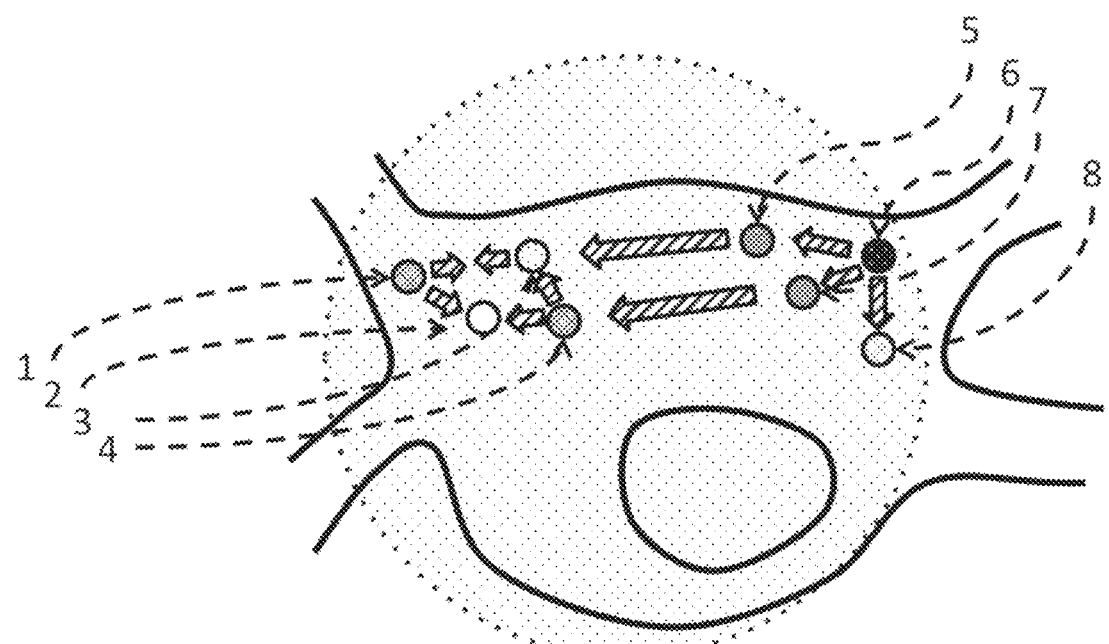

As shown in FIG. 2C, if the wavefronts emerging from the vicinity of electrode 7 are at a higher frequency than those emanating from the vicinity of electrode 1, it may be that aliasing occurs and activation of electrode 4 is falsely attributed to ultimately be coming from electrode 7, as illustrated by the striped arrows. In turn, this ascription may impact on the ascriptions of activation of electrode 1 to 3, and these may be falsely assigned as being predominant followers rather than predominant leaders. In the diagram, electrodes are represented as leaders by increased shading and followers by reduced shading. Electrode 1 is particularly affected, being ascribed as being only leading in a low proportion of activations.

Figure 2D:
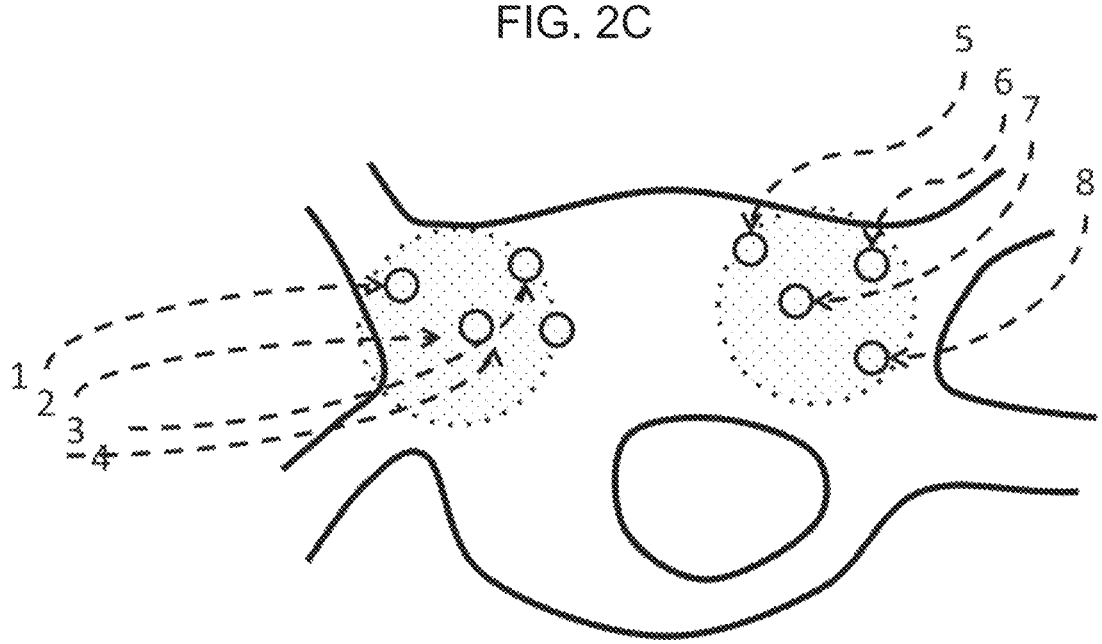
Figure 2E:
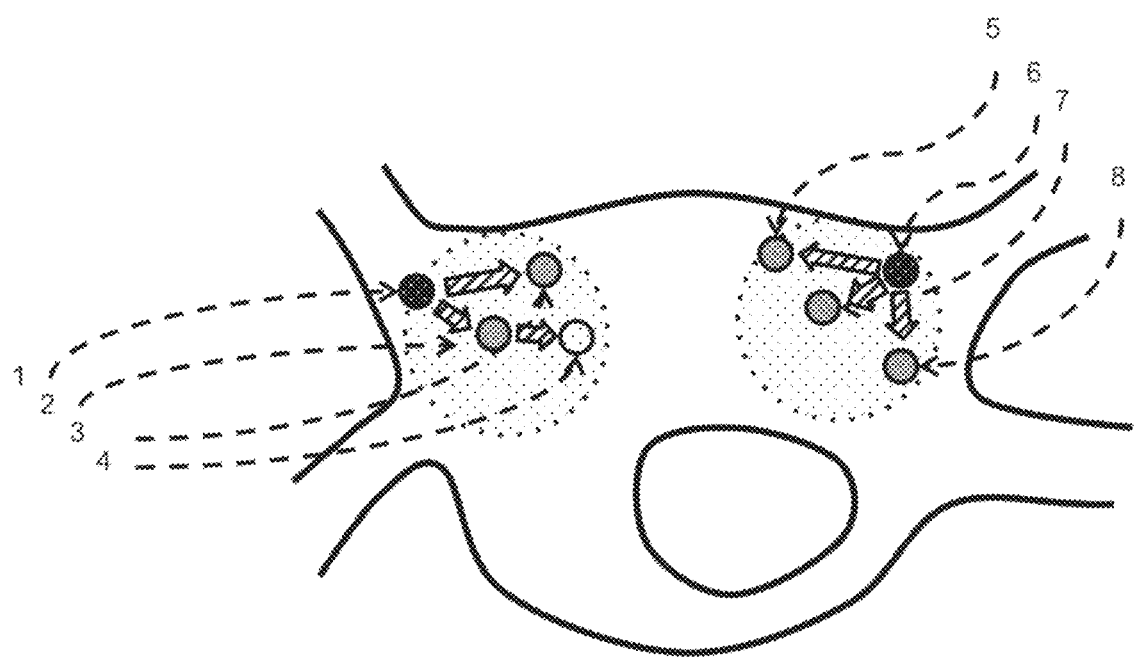

FIG. 2D on the other hand depicts a situation whereby only a small geodesic distance is used for calculations. Here, it can be seen that an electrode is compared to fewer and more local sites than in the previous example. FIG. 2E shows the resultant vectors of activation calculated, as electrodes 3 and 4 are no longer compared to electrodes 6 through 9 due to the narrower geodesic distances employed, effects of aliasing are thus mitigated and eliminated.

Figure 3A:
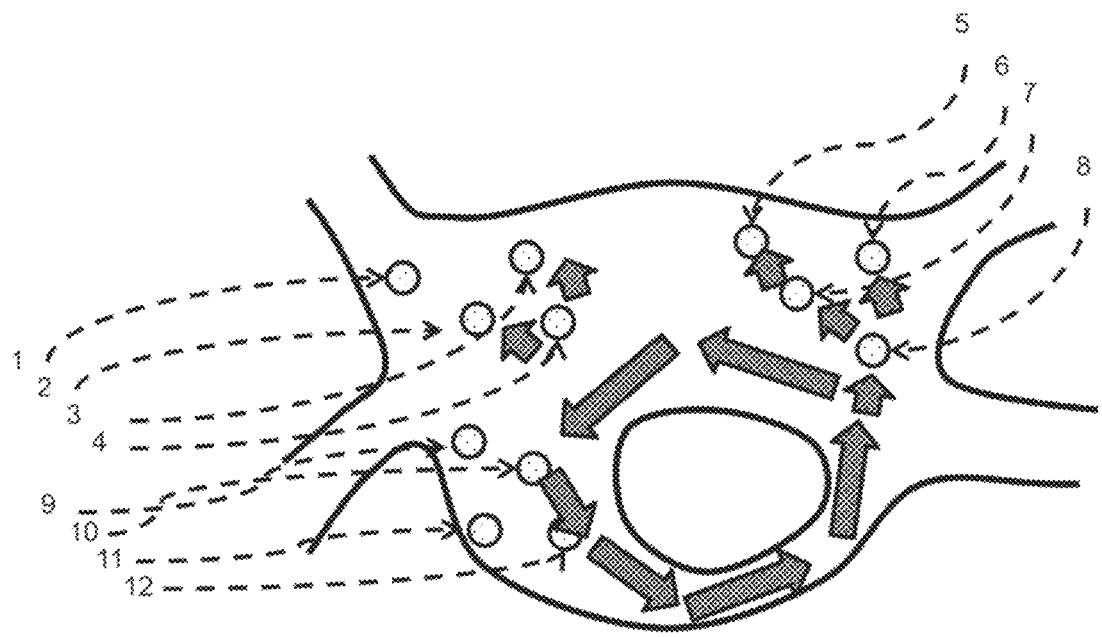
FIGS. 3A-3D show a further example of measurements taken by electrodes and how geodesic distance affects this, in this case in response to an arrhythmia with an anticlockwise circuit around the mitral valve ring.

FIG. 3A depicts an alternative example of an arrhythmia with an anticlockwise circuit around the mitral valve ring. Electrodes 1 through 9 remain in the same positions, and electrodes 10 through 13 are now placed on the septum.

Figure 3B:
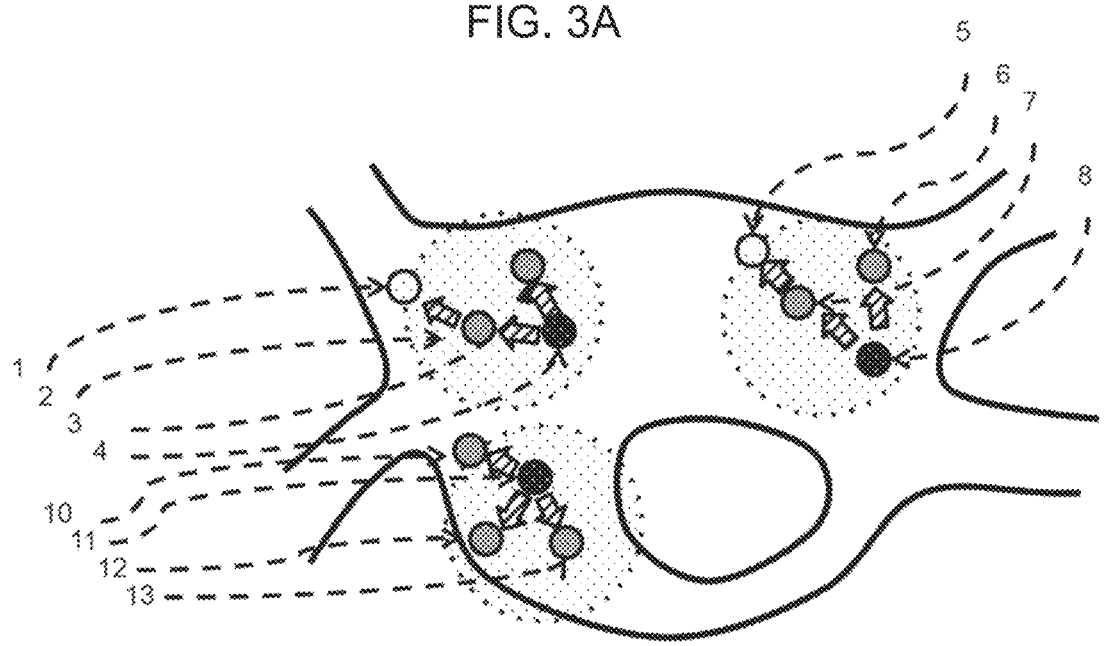

As shown in FIG. 3B, when a small geodesic distance is used, each group of electrodes (1-4, 5-9 and 10-13) is treated individually, giving the impression of multiple leading sites, rather than the ground-truth of a single macroreentrant tachycardia. Although such a small distance has some utility in that it tends to locate points within the critical circuit, it does not give any indication of the circuit direction.

Figure 3C:
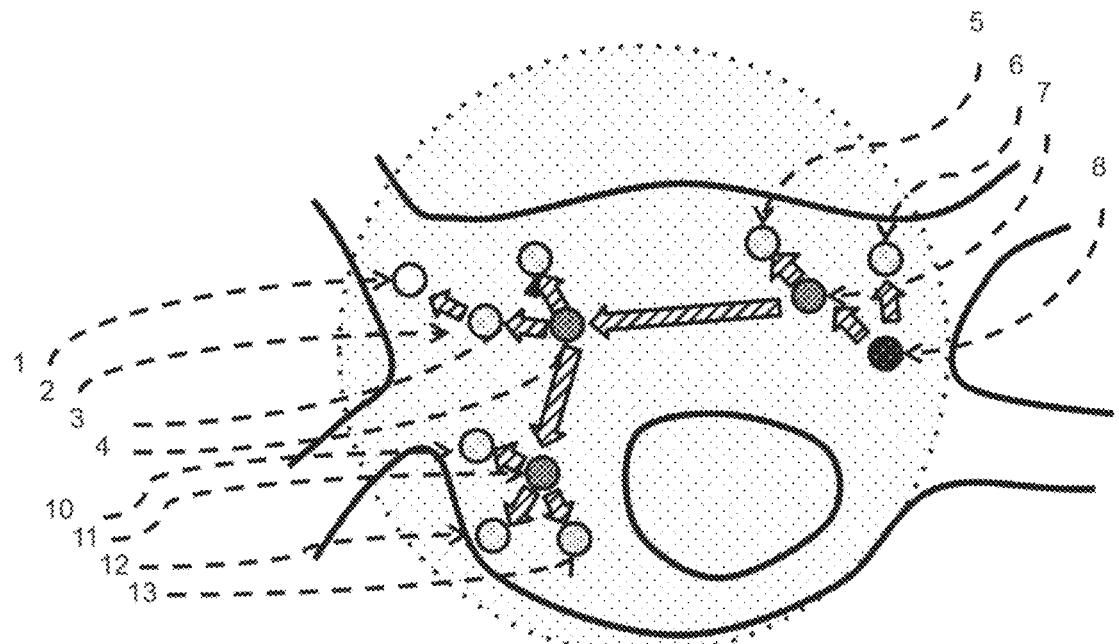

Alternatively, FIG. 3C shows a comparative example where a larger geodesic distance is used. In this case, each group of electrodes (1-4, 5-9 and 10-13) is considered in an overlapping manner to other groups. A single circuit is therefore identified going anticlockwise across the anterior wall. In this example the posterior wall is not mapped, but would show progression of activation in the opposite direction to the anterior wall, completing the circuit. The decision as to how a geodesic distance is set is made on a combination of the regularity of the underlying rhythm and the cycle length. Machine learning will further refine and resolve this process.

Figure 3D:
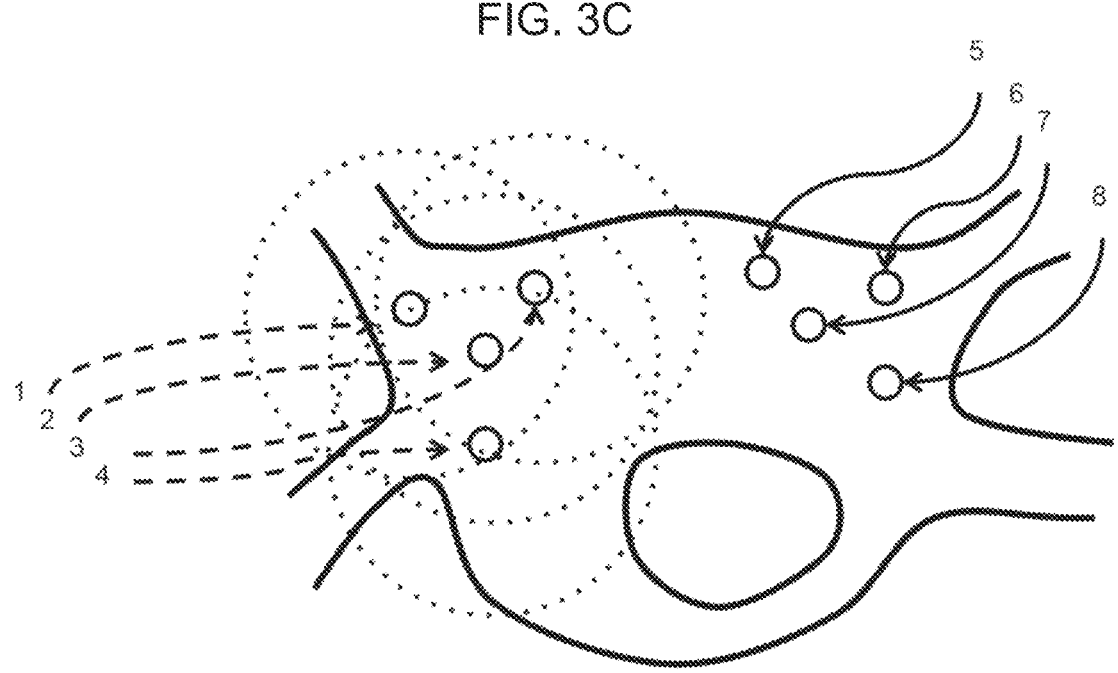

Finally, FIG. 3D shows a further example in which multiple areas of comparisons for each electrode selected with its own geodesic distance for comparison with other electrodes. Electrodes 1 to 4 are compared with one another, electrode sites 6 to 9 are also compared to one another (geodesic distances here not shown), but each group lies outside of each other's areas of comparison so are considered as distinct groups in this example.

ii) Activation Times and Pole Leaders

Drivers of AF have in a majority of studies not shown complete stability during the recording. However, these have shown to be repetitive and recur at the same anatomical site. Considering both this and the chaotic nature of AF the STAR-mapping system works to determine the proportion of time an electrode pole is leading in relation to its consecutive pole pair. Local electrogram activation timing may be determined through identifying the steepest descent on a unipolar electrogram i.e. the maximum negative deflection in the signal (dv/dt), by identifying the predominant peak on a bipolar electrogram, but identifying the maximal phase change of a unipolar or bipolar signal or by other methods. Comparing the activation times obtained, the electrodes in the pair can either be labeled as a follower or a leader depending on the activation time and interval. For example when considering electrograms recorded from closely spaced electrodes A and B if the interval between A and B is shorter than from B to A it is considered that A is leading B. However if the interval between A and B is so short as to be physiologically impossible then either the B is leading A, or if the time from B to A is also physiologically implausibly long then the activations are unrelated. These parameters may be adjusted according to the data acquired during the procedure and a priori knowledge gained from previous cases. For every electrode location, the overall propensity to be a leading pole is calculated from the proportion of times it is determined to be a true leading pole across every pair to which it contributes. This is to say that a pole can only be a 100% leader if it is activated ahead of all poles it is paired with. Along the same line a pole will be leading 0% of the time if it is consistently following the other pairs.

It will be appreciated that for each electrode location, a plurality of lead signal scores may be calculated, for example, it can be assigned a score for each discrete activation at that electrode, for each time analysis window where calculations are performed, for each series of groupings by activation sequence, for each overlapping area from where signals were acquired and so on.

The final single lead signal score for a specific location therefore represents a statistical measure of the proportion of time that location may be considered to be leading, which may be corrected or normalised to recording time periods, cycle lengths, numbers of activations recorded, numbers of overlapping areas recorded and so on. This final single lead signal score may be further subdivided and recalculated depending on groupings of activations sequences.

Figure 4A:
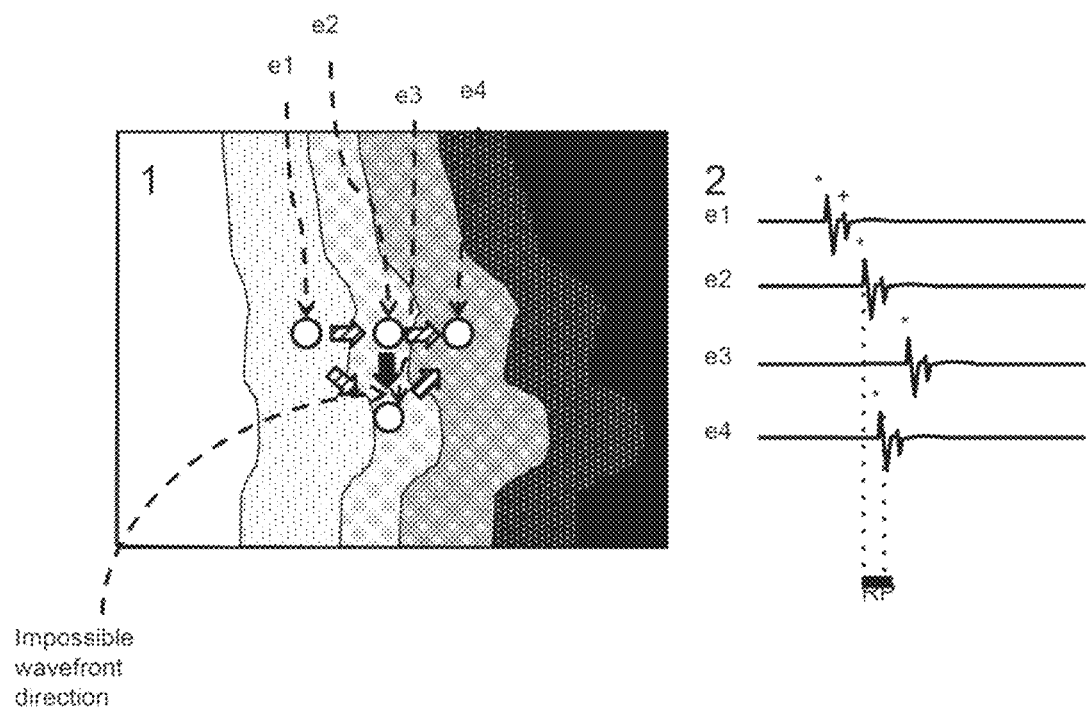
FIG. 4A depicts the effect of physiological parameters in determining refractory periods.

When determining activation times, to ensure the same activation sequence producing local and far-field electrogram deflections on the electrode and thus potentially counted as two separate activations of that electrode, filtering using refractory periods is used. If the activation of the electrode falls within this refractory period it cannot be representative of a separate activation, as within this time period the atrial tissue cannot be re-stimulated by another activation. Thereby the second activation is seen as being part of the initial activation sequence and is disregarded by the system (FIG. 4A). Previous studies on mapping complex fractionated electrograms have regarded <70 ms as an approximate effective refractory period of atrial myocardium whereby anything seen within this time is unlikely to be a second wavefront. This is consistent with the refractory periods obtained during AF in animal studies.

Figure 4B:
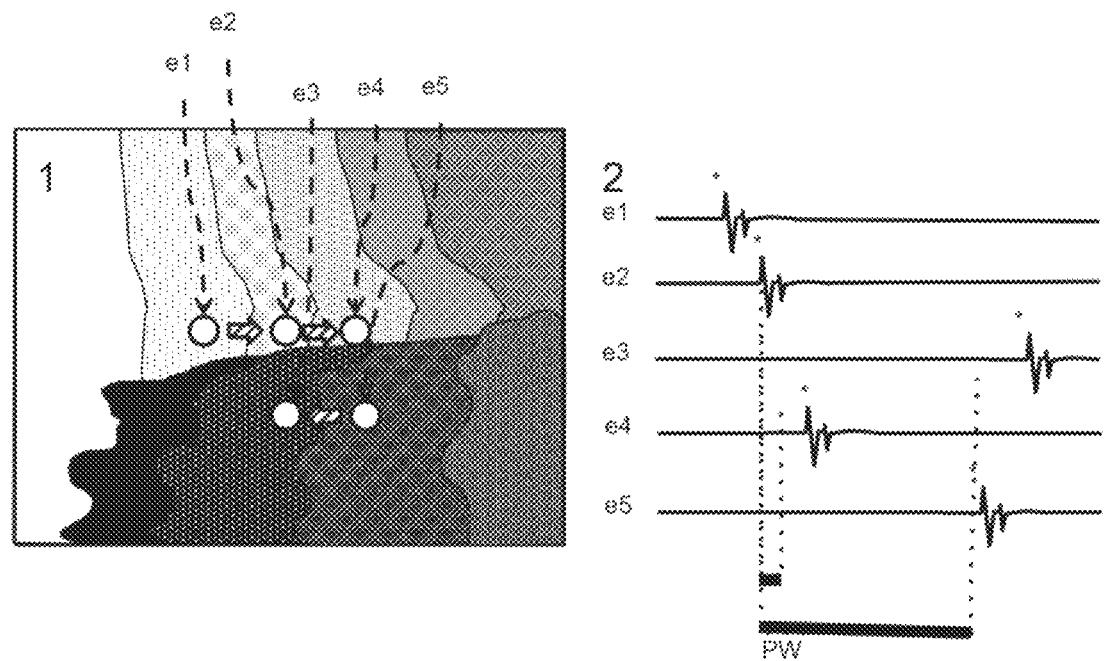
FIG. 4B depicts a similar wavefront to FIG. 4A, however in this example a wavefront is seen progressing this time from right to left on the inferior portion of the area shown.
Figure 4C:
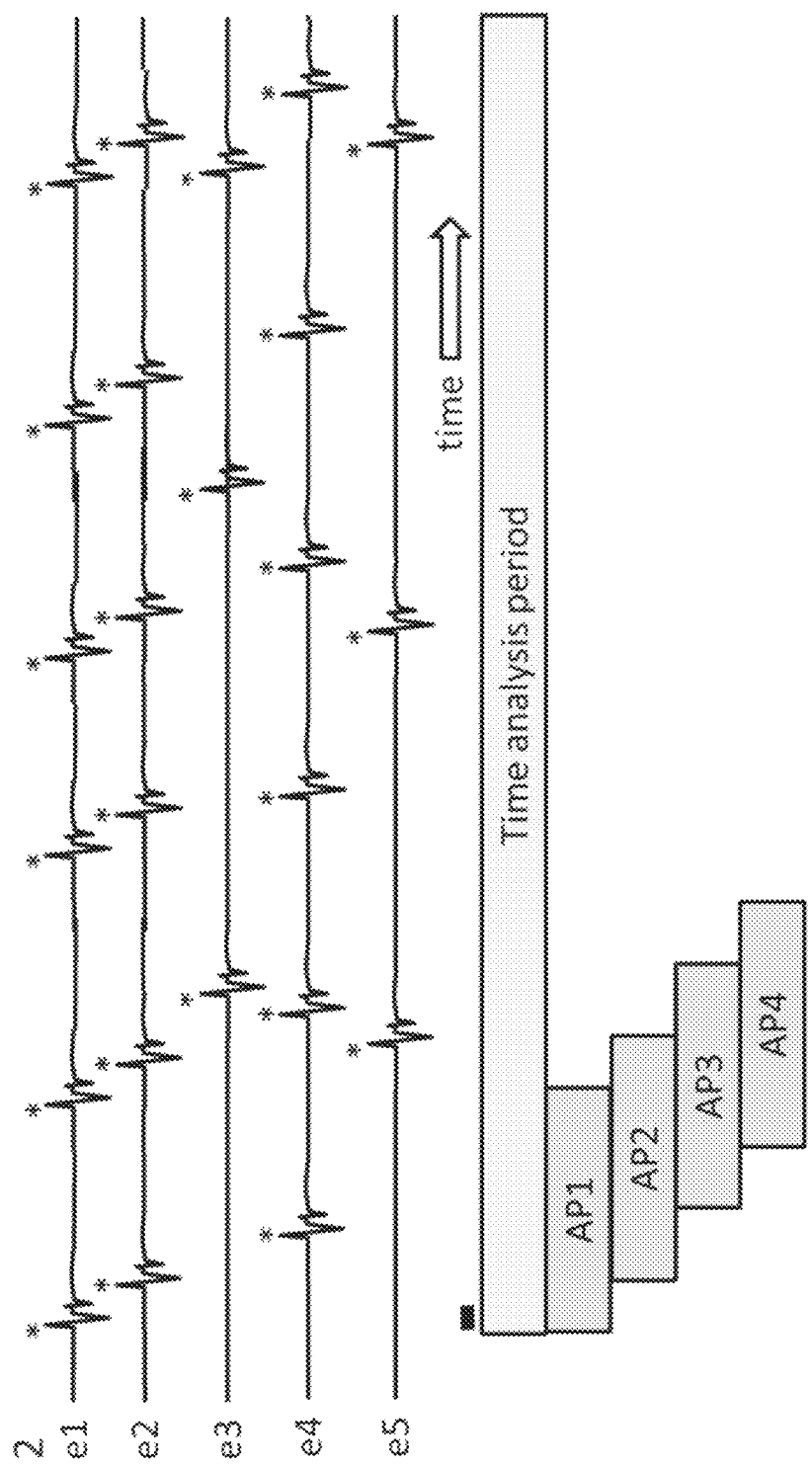
FIG. 4C shows an example of multiple overlapping analysis periods within a time analysis period.

The effect of physiological parameters in determining refractory periods can be better understood with reference to FIGS. 4A-4C. Referring first to FIG. 4A, panel 1 shows a region of excitable tissue, where a wavefront is moving across from left to right. This is represented by isochrones of increasing shade indicating later activation. A group of 4 electrodes may be considered in this example, labeled e1 to e4. Representative electrograms are shown in panel 2. In this example, prior to comparing which electrode is leading each, the activation time of each electrode is identified (marked as *) the subsequent electrical deflection (marked as +) on electrode e1 is too close in timing to the previous marked one and therefore not considered as a separate activation. STAR Mapping would consider e1 to be leading all the other electrodes, and e4 following all other electrodes. However, e3 only very slightly follows the activation time of e2 as their orientation is roughly perpendicular to the wavefront of activation. The conduction velocity that would be required for the wavefront activation at e2 to be conducted to e3 directly is unfeasibly high, as conduction velocity is given by distance/time and the time difference between the two sites is small. The refractory period between these two sites can be calculated using an arbitrary or calculated maximum conduction velocity, giving rise to a refractory period (RP). Therefore the STAR mapping system will determine that the activation cannot be progressing from e2 to e3 (this wavefront direction is labeled with a black arrow with legend "impossible wavefront direction") rather the activation at e2 and e3 are either from separate wave fronts approaching from different directions or as a result of a single wavefront crossing e2 and e3 at the same time. Further collection of data from locations nearby or over different time periods will help to resolve which of these two possibilities is the correct one. Apparent conduction vectors are shown by the striped arrows in panel 1.

FIG. 4B illustrates a similar wavefront to FIG. 4A, however in this example a wavefront is seen progressing this time from right to left on the inferior portion of the area shown. This would be likely to be a progression of the wavefront on the upper half of the figure, curling clockwise on the right hand side to change direction. Here, an extra electrode site, e5, is illustrated for clarity. There is now a very great time difference from sites e1 and e2, to e3. Now considering the conduction velocity equation above, the time difference between these sites is too long to be considered physiologically possible (i.e. is not within a physiological window, PW), and therefore conduction will not be considered from e1 or e2 to e3. e5 would be considered to conduct to e3, and the two limbs of the wavefront may be considered as separate wavefronts unless the time difference from e4 to e5 is within physiological limits.

FIG. 4C depicts multiple overlapping analysis periods (AP1 etc) within a time analysis period. For each analysis period, multiple electrode comparisons are made as to which electrode is leading which. In this example 5 electrodes signals from within a geodesic distance are shown with activations determined by the asterisks. In AP1, e1 is seen to lead all other activations. This pattern continues, but occasionally e5 leads e3, yet there are far fewer activations of these electrodes than of e1, e3 e4. The overlapping analysis periods produce a number for each AP which indicates the number of times that that signal leads other signals within that AP. All AP scores for each electrode are then combined after analysis of the entire time period to produce a single signal leading score for each electrode location.

To ensure an electrode or location is accurately labeled as the leading electrode or location it is important to ensure the electrodes are recording the same activation sequence (or wavelength) and one of the electrodes in the pair is not activated by a different activation sequence. As several studies have suggested some arrhythmia (including AF) may consist of multiple wandering wavelets with a re-entry mechanism it is highly possible that the paired electrodes are recording separate wavelets with no mechanistic relation. To overcome this the activation time differences between the electrodes are reviewed. To retain differences that are feasible and filter out those that cannot be related to each other, the geodesic distance between the electrode pairs is used and together with the conduction velocity (CV) a plausible activation time difference is determined. For the purposes of illustration, let us consider two electrodes positioned in the heart, electrode A and B with distinct activations on them. If the activation time difference between electrode A and B is smaller than the limit set by the STAR mapping system then is it unlikely that pole A and B are activated by the same activation wavefront and thereby these signals are rejected by the system.

Several studies have looked at CV in the human LA both in sinus rhythm and AF. It has been established that CV vary in areas with normal voltage (indicating healthy tissue) compared to low voltage zones (LVZs) which indicates scarring. It has also been shown that CV has a negative correlation between bipolar voltage and proportion of LVZs. As a result the bipolar voltage map and proportion of LVZs influences the CVs used in the STAR system.

iii) Creating and Interpreting a STAR Map

The STAR mapping technique may be used with in conjunction with any electroanatomical mapping system, for example Carto 3 (Biosense Webster), Precision (Abbott Ltd), Rhythmia (Boston Scientific) connected to one or more multipolar mapping catheters. Data from more than one mapping system may be combined, for example using time-stamped electrogram data from LabSystem Pro (Boston Scientific) simultaneously with location data from a 3D mapping system. Data requirements in order to perform this method are: i) 3D coordinates for the vertices and polygons that make up the chamber geometry; ii) 3D coordinates for the position of electrogram recordings; iii) the corresponding recorded electrogram data. The STAR mapping method may be performed on a separate system after physical data export, alternatively it may be performed on the physical computer processors and memory modules of 3D mapping systems or electrophysiology recording systems.

A typical STAR map consists of a left atrial geometry, itself a replica of the LA geometry created with any 3D mapping system, with projected sites of electrogram recording poles. A colour scheme can be applied where colors are a representation of the final leading signal score of each site, for example a rainbow scale where 100% leader is coloured red and 0% leader is coloured blue. A plethora of methods known in the art can be applied to superimpose these colours on the map, for instance an interpolated surface colouring or coloured superimposed dots. Ease of interpretation may be further enhanced by animation or variation in apparent height, diameter or colour intensity of site markings. As an indication of activation sequence, and to further aid interpretation, arrows may drawn from predominantly leading poles to its relevant pairs.

An exemplary study demonstrated that the STAR-mapping algorithm can accurately identify multiple sites of pacing in the human LA and establish the mechanism of complex ATs including both focal/micro-reentrant and macro-reentrant circuits in the right and left atria.

The STAR-mapping algorithm was extensively validated with atrial pacing in sinus rhythm from multiple sites of pacing in the human LA. The operator and blinded observers were able to determine the site of pacing from the STAR maps, the pole(s) detected as a leader(s) by the STAR algorithm, i.e. sites of earliest activation, also correlated to the pole(s) on the basket catheter with earliest activation when reviewing the electrograms. Further to this, the pole identified as a leader was also the closest basket pole to the site of pacing when reviewing corresponding CARTO maps.

The effects of alteration of the geodesic distance over which the poles are paired allows the STAR mapping method to be adaptable in consideration of previous data, supporting that drivers critical in the maintenance of arrhythmia occupy small areas of the LA and to minimise error from aliasing and multiple wavefronts. To validate the STAR-mapping system with regards to identifying complex wavefronts, STAR maps were created during AT and compared with confirmed AT mechanisms determined using conventional methods.

Figure 9A:
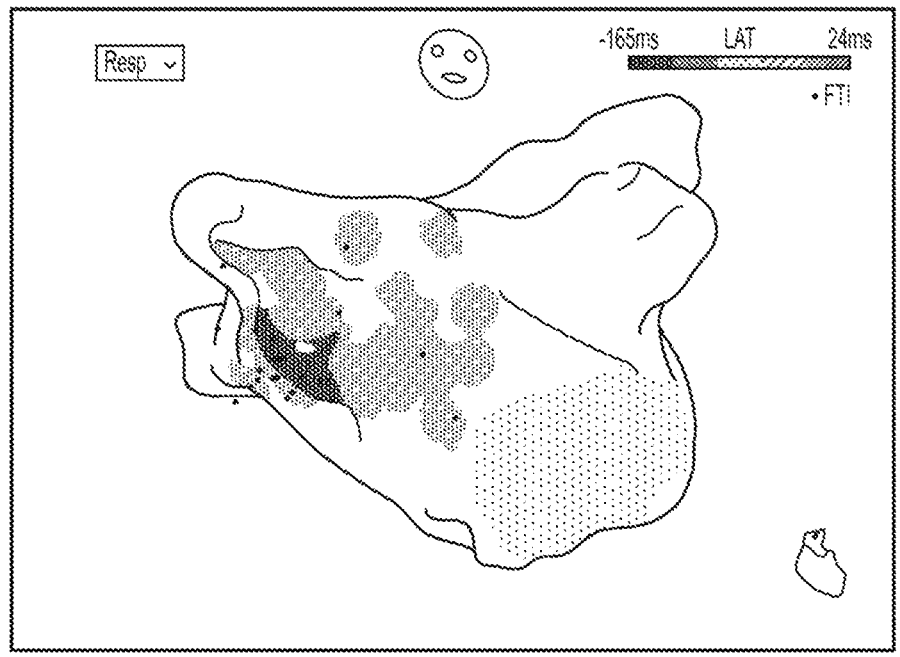
FIGS. 9A-C show examples of 3D maps produced using a method according to an embodiment of the present invention along with corresponding local activation timing maps.
Figure 9B:
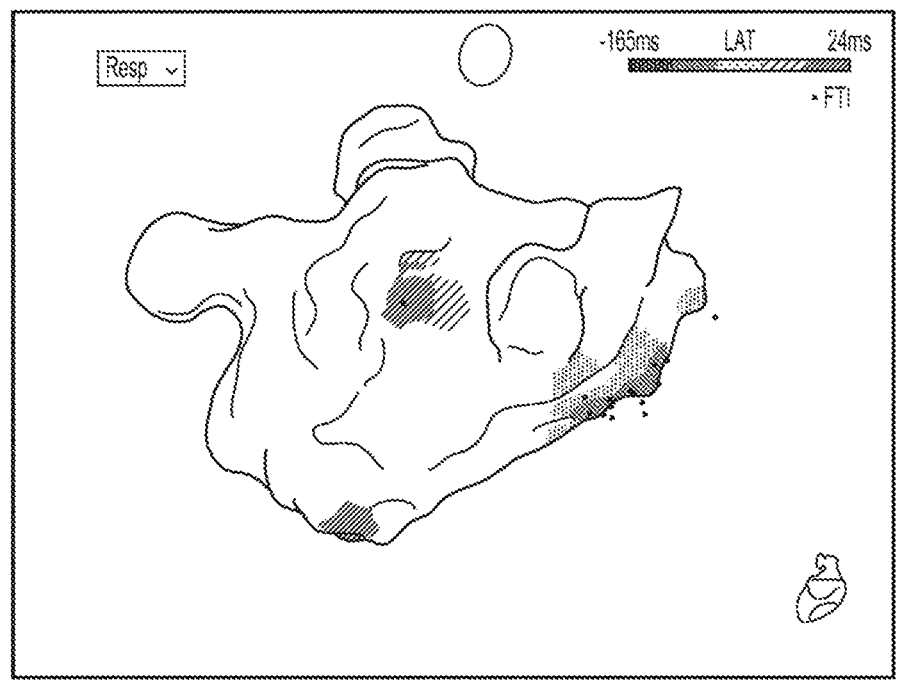
Figure 9C:
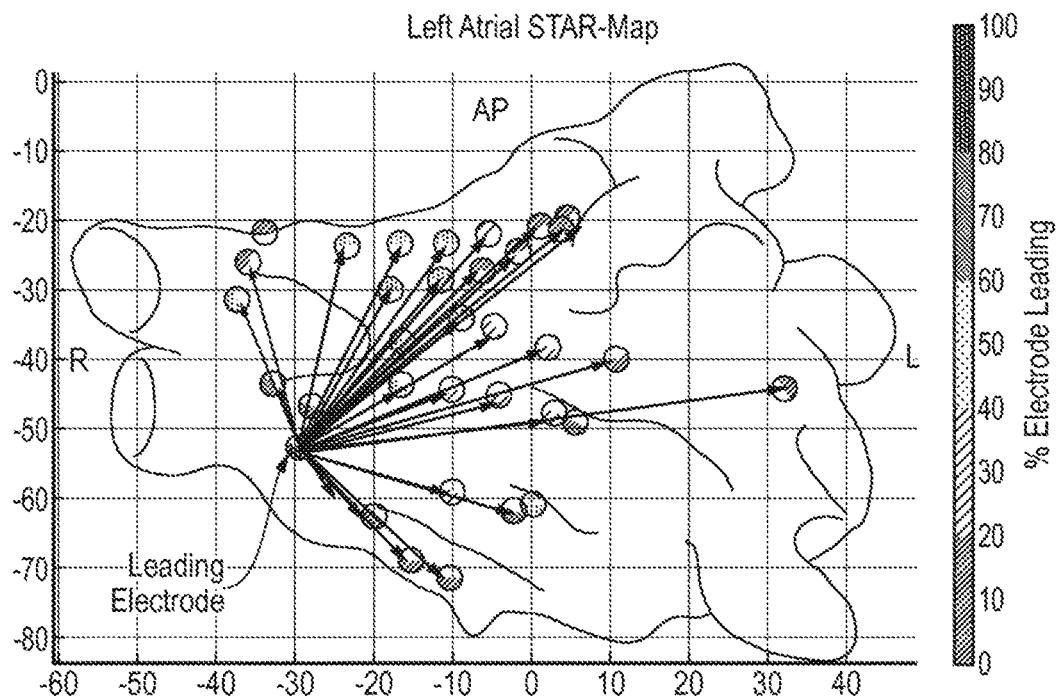
Figure 9D:
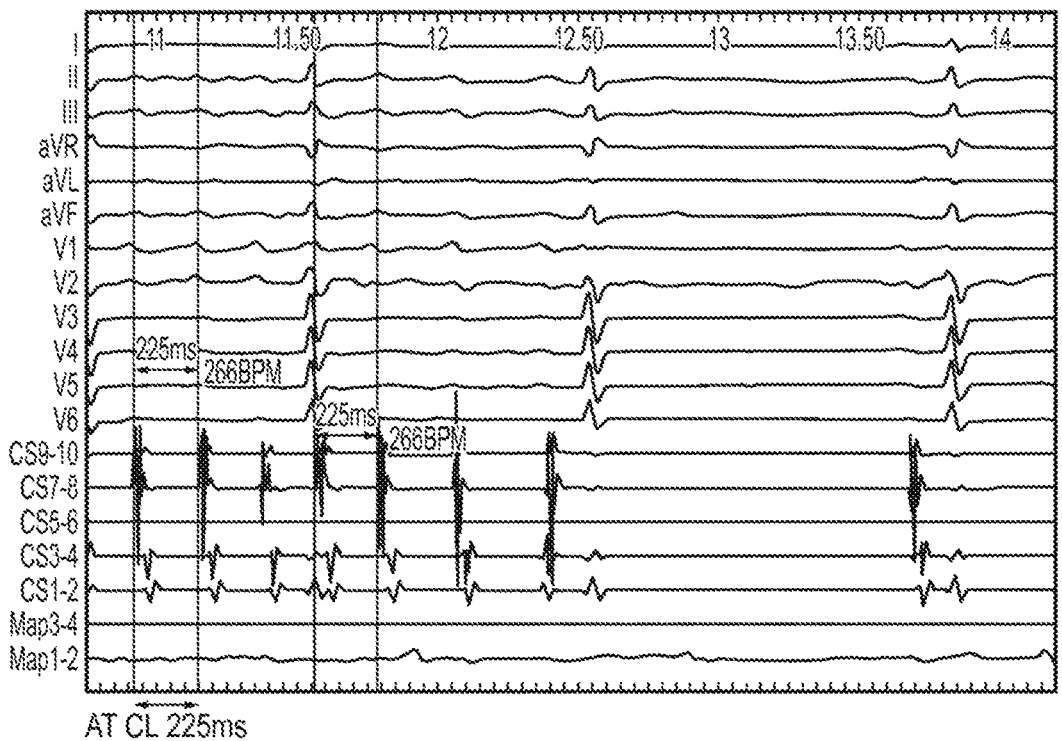
FIG. 9D depicts corresponding electrograms.

FIGS. 9A-C show the mapping of a focal AT that was mapped to the septum on the STAR map and conventional local activation time map created using CARTO. FIG. 9A is a conventional local activation time map in a titled anterior-posterior view that demonstrates earliest activation at the septum. FIG. 9B is a conventional local activation timing map in a titled right lateral view supporting the spread of the AT from the septum across the LA. FIG. 9C shows a STAR map that shows a high STAR score at the septum that correlates to the focus of the AT on the conventional local activation time maps. Finally, FIG. 9D shows BARD electrograms that include the surface ECGs, CS and Map electrograms that shows an AT with a CL of 225 ms terminating to sinus rhythm on ablation at the site of high STAR score.

The effects of altering geodesic distances for mapping is demonstrated in this example. Geodesic distances above 6 cm result in maps where recording sites from separate anatomical surfaces may be paired with one other, which is physiologically unfeasible. Such high geodesic distances for comparison should therefore preferably be avoided. Similarly, excessively small geodesic distances for comparison (e.g. <3 cm) causes excessive segmentation of anatomical surfaces. This causes multiple poles affected by the same local driver to not be compared with one other, and excessively high number of poles may be assigned high signal leading scores as a result. Multiple leading poles may falsely be identified and an indication of an excessively wide area requiring ablation follow.

Figure 8:
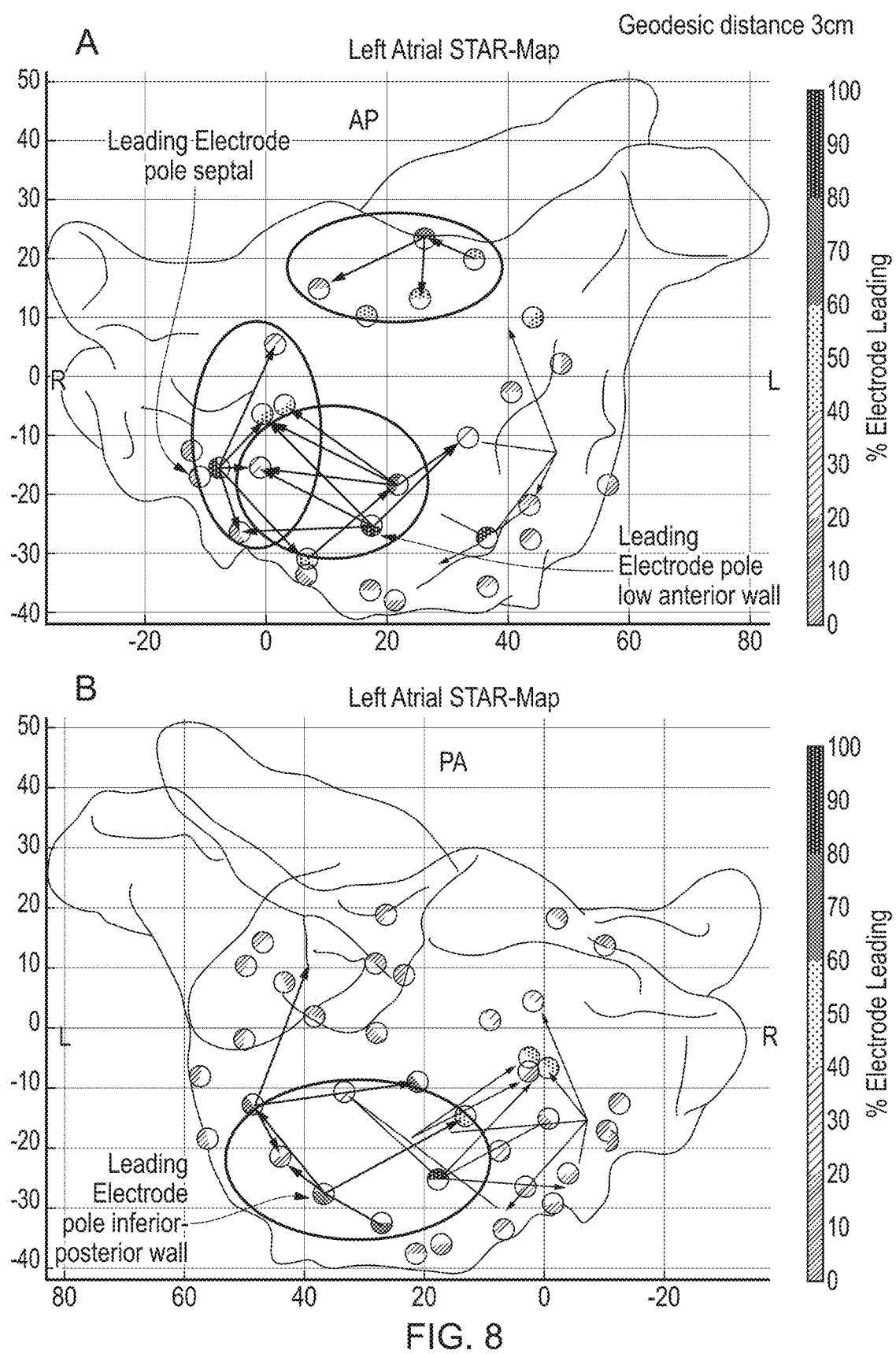
FIGS. 8A-8D show examples of 3D maps produced using a method according to an embodiment of the present invention.
Figure 8:
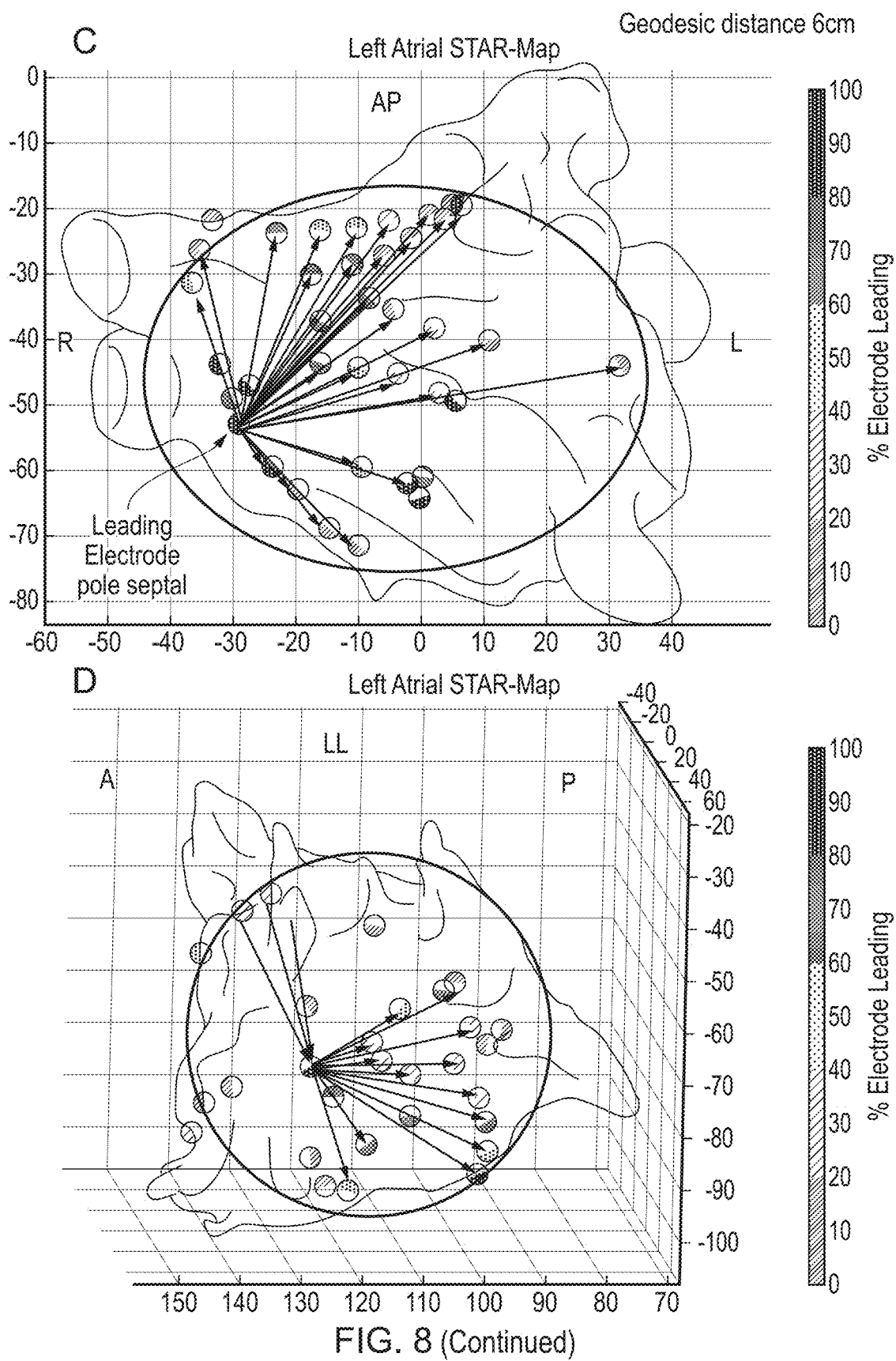

As an example, FIG. 8 shows a STAR LA map where a geodesic distance of 3 cm was used during the pairing of the basket poles during mapping in AF. This pairing allowed the LA to be segmented into sections. In an anterior-posterior (AP) view (FIG. 8A) two sites of high STAR score poles were identified, septal and low anterior.

FIG. 8C shows a STAR LA map in an AP view where a geodesic distance of 6 cm was used during the pairing of the basket poles. The map demonstrates a focal AT with slow cycle length (>300 ms) mapped to the septum with the high STAR score correlating to the site of the AT. The same tachycardia with a short geodesic distance (FIG. 8C) will show multiple drivers all at the edge of the area mapped as determined geodesic distances other than the location overlying the source which shows the source in the middle of that geodesic area. While this is interpretable it is more complex to interpret than FIG. 8B.

FIG. 8D shows a STAR LA map where a geodesic distance of 6 cm was used during the pairing of macroreentry AT. The map demonstrates a macro-reentrant AT whereby poles anteriorly are leading poles posteriorly as a result no high STAR score pole is identified with no pole leading 100% of the time as seen with a focal AT.

The simplified method of calculating a STAR map shown in FIG. 10 will now be explained. Five electrogram pairs are shown, (a-e), and the electrograms derived from each electrode are shown below. Three representative patterns which together comprise 80% of the total recording time are shown (panels i-iii). In panel (i), accounting for 50% of the time electrode a is leading all other electrodes. In panel (ii) a different activation sequence is illustrated, with electrode (c) leading, accounting for 20% of the time. Panel (iii) is another activation sequence where electrode (e) leads, 10% of the time. Each electrode has a value associated with it based on the proportion of time that electrode is seen as "leading" is closest associated electrode as shown in panel (iv). A final process combines these data and superimposes these on a combined map, highlighting the leading electrodes for example with colour coding of electrode leading proportions.

Figure 5:
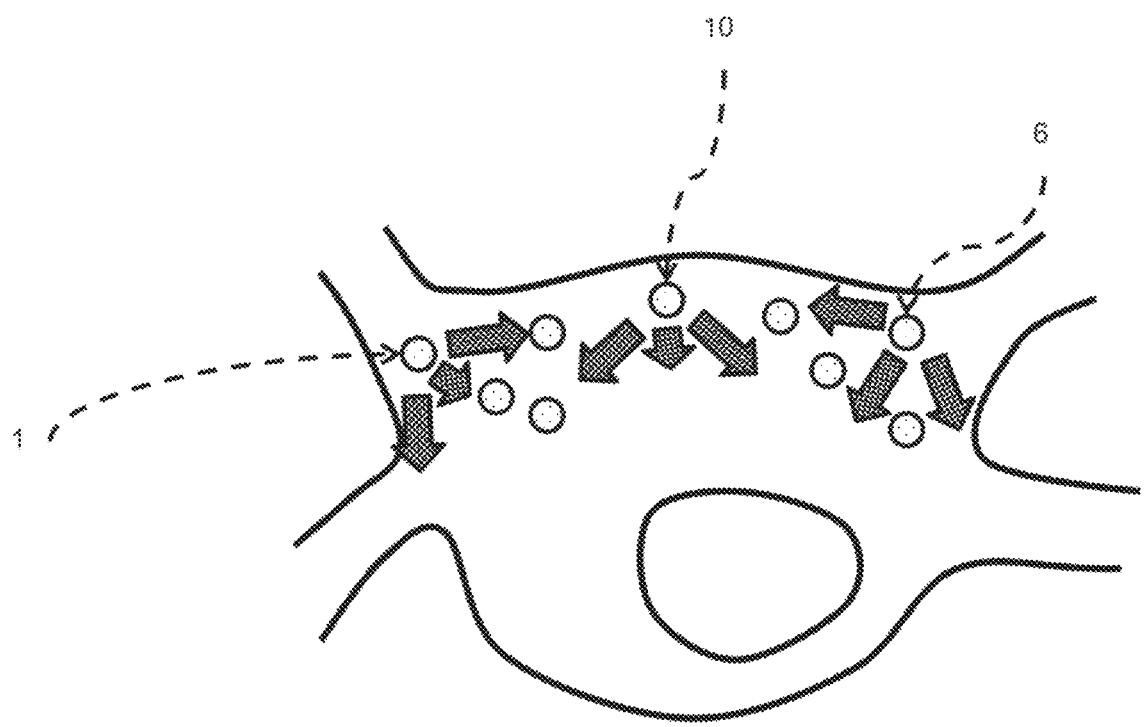
FIG. 5 depicts illustrates how a STAR mapping embodiment of the claimed method assigns a proportionality to leading scores having already discarded activations and activation vectors using the algorithms derived from plausible biological physiology.
Figure 6A:
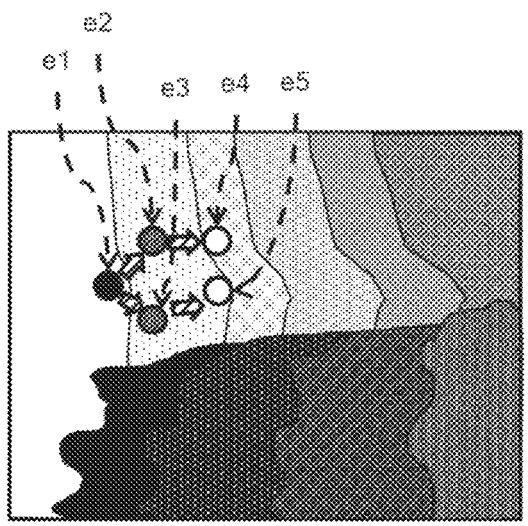
FIGS. 6A-6D illustrate how sequentially acquired sites may have their leading signal score assignments combined.
Figure 6C:
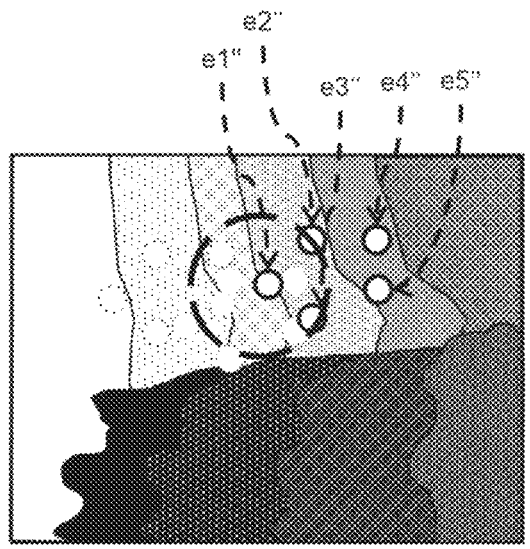
Figure 6B:
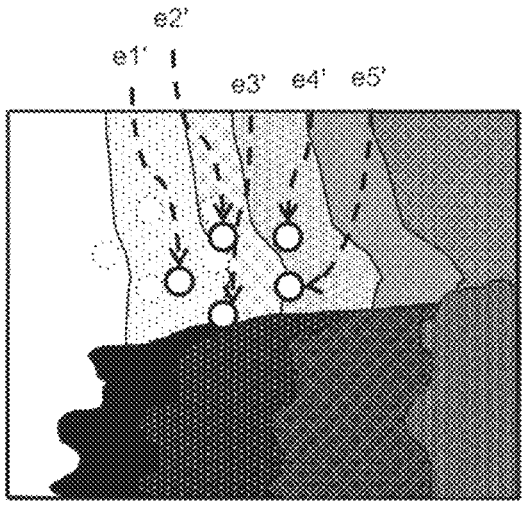
Figure 6D:
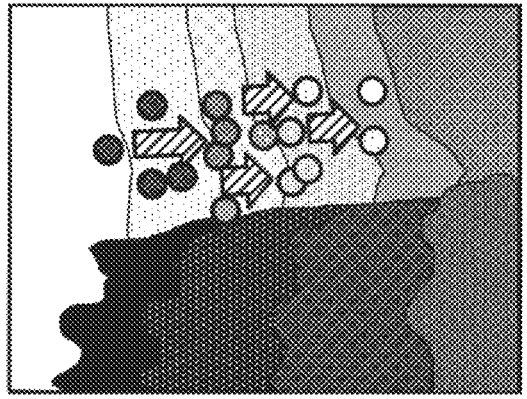

FIG. 5 illustrates how STAR mapping assigns a proportionality to leading scores having already discarded activations and activation vectors using the algorithms derived from plausible biological physiology described in FIGS. 4A-4C. Consider the situation whereby three electrode sites, here e1, e6 and e10, are close to driver sites. The chaotic activations inherent to atrial fibrillation cause, for example, e10 to be leading a local area of activation only 40% of the time, and e6 to be leading only 20% of the time. The leading signal score will be assigned in relation to the proportion that area is seen leading the local activations following comparisons within geodesic areas. These signal scores may be further amended by a plethora of factors, such as whether they are consistently early after a pause in arrhythmia cycle length for example, or by other weightings applied by machine learning.

FIG. 6 illustrates how sequentially acquired sites may have their leading signal score assignments combined. Consider an excitable surface which undergoes mapping with electrodes e1 to e5 in FIG. 6A. A series of signal leading scores are generated over a period of recording time using the star method. The electrodes are now repositioned to positions e1' to e5' and the process repeated, shown in FIG. 6B. A series of new signal leading scores are generated at these new sites. The new signal leading scores at the e1'-5' sites can be related to those previously acquired by, for instance normalising to a common electrode location, or if in the case no location is common to both mapping sites and areas are not overlapping, normalising to a interpolated score. A region in which electrodes are very close, overlapping or interspersed with previously acquired positions may be determined, and new signal scores from the new position may be related to those signal scores from previously acquired positions. For example, in FIG. 6C, location e1" is in a location that was previously bounded by the electrode sites inscribed by the dashed circle, previous sites are shown as white dotted circles labelled as before. Assuming recording times at each site are of sufficient length to establish a true local lead signal score, the newly acquired signal score from e1" may be related to signal scores from e4, e5, e2', e4' and e5', and all signal scores recalibrated to a common relative scale. This may be by linear interpolation, pattern matching or other methods. e2" through e5" may be thus rescored by their relationship to the now calibrated score from e1". By repeating this method, the entirety of a surface may be mapped with distributed electrode sites. FIG. 6D demonstrates how such sequential mapping over several acquisitions may build up a larger area of coverage of signal scores related to one another, and how an overall wavefront direction may thus implied as shown by the striped arrows.

Figure 7:
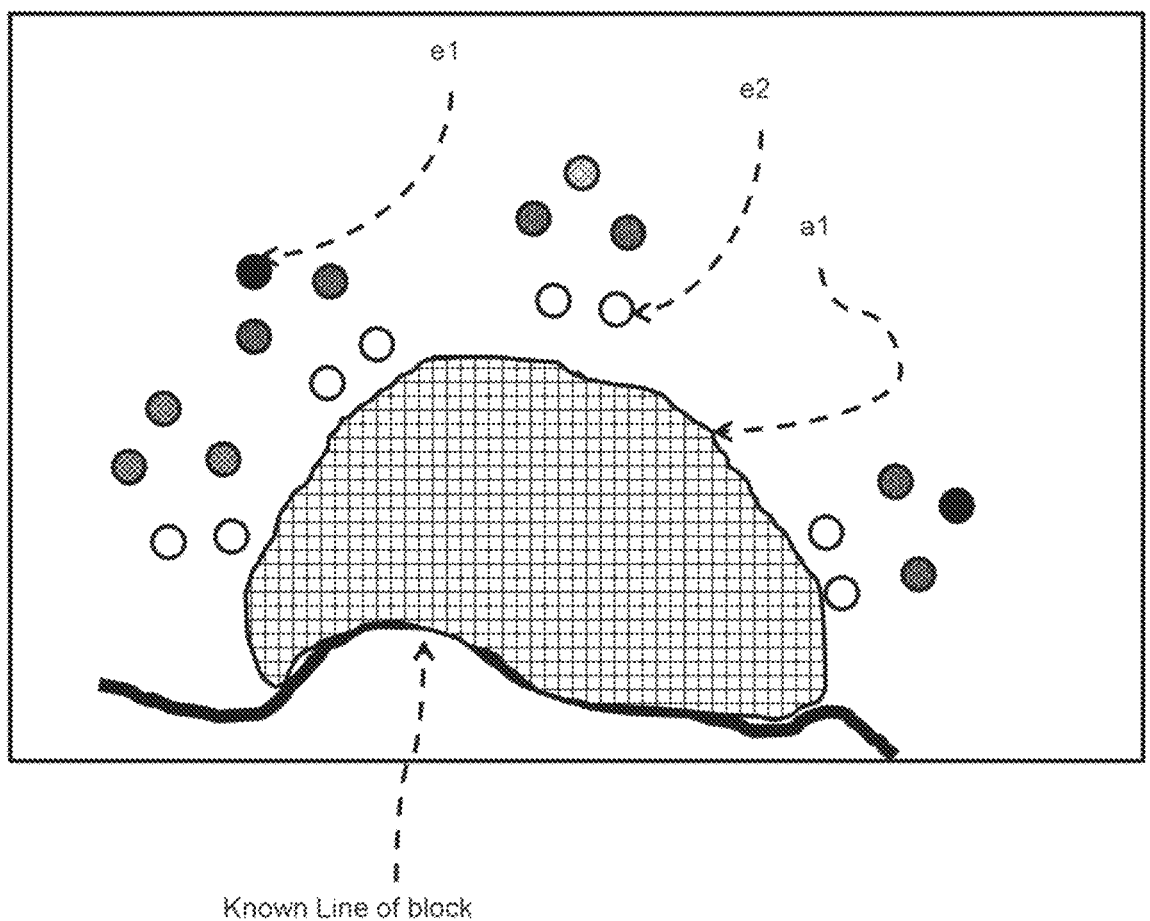
FIG. 7 is a schematic diagram depicting an area with low signal scores in which driver areas are unlikely to be found.

FIG. 7 shows an example of an area with low signal scores in which driver areas are unlikely to be found. Here, an area of excitable tissue is mapped by several electrodes, represented as circles. Each is assigned a signal score, with darker shading representing higher signal lead scores, with electrode e1 for example representing a leading signal. An area is circumscribed by electrode locations exhibiting low lead signal scores, for example, e2. This area may be bounded on one aspect by a known line of block (thick line) which may be a valve structure, scar, ablation line or other cardiac structure. As this area is bounded by sites with low signal scores, it can be inferred that this area does not contain a driver area and therefore does not need to be mapped in detail. Such an area is represented here by the crosshatched area.

The above description has focused on the core components of STAR mapping. However, there are other original facets which may be incorporated into the system detailed below.

Far Field Mapping

Far-field electrograms are electrical activity recorded at an electrode despite that electrical activity occurring some distance away. This is conventionally discarded where possible by mapping systems. These may be differentiated from near-field electrograms (electrical activity occurring local to that electrode) in several ways. Far-field electrograms are usually less 'sharp', having a low frequency appearance, and digital filtering of electrogram signals may allow their removal. Secondly, the far field electrogram may be identified as corresponding to another electrogram, for example a far-field electrogram representing ventricular signal during an atrial signal might correspond to the QRS complex denoting ventricular activity on the surface ECG. A further method for identifying whether a signal component is local or far-field is to utilise the unipolar signal to identify a significant signal component earlier to the defined activation component. In this manner, it becomes possible to define across certain anatomical sites, whether an area outside of the local area of mapping is in fact driving the tachycardia, and gradients of these far-field electrograms may be compared to establish the likely anatomical location requiring further mapping. This may be applied by identifying an early unipolar low frequency signal in a leading site, and comparing a defined metric of this signal, for example the unipolar signal amplitude, with other paired and synchronously acquired electrograms exhibiting this signal. A gradient of these amplitudes will be apparent, with higher amplitudes closer to the origin of the far field signals. Thus a gradient in these far-field signals may indicate the source of arrhythmia, for example identifying far field right atrial signal recorded on an electrode in contact with the left atrial septum.

There are three further facets to the system to refine this initial prediction regarding which sites are and are not important in maintaining AF:
(i) Sense checking algorithms
(ii) Modifying factors
(iii) System feedback Sense Checking Algorithms Electrograms are provisionally timed and wavefronts are presumed to travel in directions that are plausible based on conduction velocity and refractory periods. Three mechanisms to sense check the initial predictions by the STAR system, which may be used to amend signal leading scores.

Firstly, for any surface activated by the same wavefront, a one-to-one relationship of activations at all electrodes on that surface should exist. Therefore, the first of the sense check algorithms looks for such a relationship between signals recorded at electrodes for any mapped wavefront. Where this is not present, such sites will not be considered to be activated by a single wavefront.

Secondly, during arrhythmia there is often subtle changes in cycle length from one cycle to the next which is often termed 'wobble' in the cycle length. This is particularly marked in AF and is one factor that makes AF impossible to map by conventional methods. A localised source generating wavefronts is presumed to be repetitive when it occurs, albeit intermittent and inconsistent. After predictions regarding wavefront movements and likely sources, an analysis of cycle length wobble during wavefronts presumed to be important may be performed. Any cycle-to-cycle change in cycle length may be assumed to occur first at an origin of repetitive wavefronts. As the wavefront moves from the source, such a cycle-length change may be detected at sites moving further from the source. This may be determined by frequency analysis, where a series of cycle length variations emanating from a prospective site may be interpreted as a coded signal, in a similar way to a defined chirp or otherwise encoded signal broadcast may be used in radio direction finding to confirm that this is the signal of interest. The directionality of wavefronts emanating from the source may thus be compared over several cycles with confirmation that they are indeed arising from that one source. Application of cycle-to-cycle variation or "wobble" logic can be applied to electrograms with reference to the geometry and results of STAR mapping to confirm mapping analysis.

Thirdly, a typical pattern of activation will occur across the heart when activation of the chamber is by a particular driver site. When a dominant activation is occurring, a defined and signature pattern of activation sequence may be observed. This can be exemplified by repetitive and varying activations typically seen in electrodes, for example within the coronary sinus. These patterns may be utilised and classified to group activation patterns together, and thus allow a series of maps to be created. Each of these maps would correspond to a greater or lesser degree to each of the activation patterns generated by each of the drivers areas identified.

Modifying Factors

STAR mapping provides a signal leading score for each of the mapped sites around the chamber undergoing mapping. These scores may be further amended by incorporating a number of weighting criteria increase or decrease the importance attached to the areas mapped as important. Typical weighting factors may be drawn from known literature or from previously acquired data. These include arrhythmia cycle length, cycle length stability (e.g. standard deviation of cycle length), dominant frequency, regularity index and organisation index, unipolar or bipolar voltage, anatomical site.

Feedback Systems/Machine Learning

Signal leading scores may be further modified by intraprocedural feedback. This will associate positive responses to ablation and a successful outcome with the ablation delivered and permit continual adaptation of the weight placed on the different sense checking algorithms and the relative importance of the different components of the weighting criteria.

The first of these feedback mechanisms is essentially intraprocedural. Through analysis and monitoring of arrhythmia cycle length, a slowing or organisation can indicate a positive response to ablation at a particular site. Such feedback can be used to modify signal leading scores, and by collating feedback from similar patients and responses to ablation, statistical models generated which themselves can be used to adapt signal scores in future patients, for example through machine learning.

Factors known to impact on the clinical success of AF ablation can also be used as feedback to such models, including different measures of clinical success where available. Exemplary clinical markers of success would include data sources and technologies such as clinical success or recurrent arrhythmia as manually recorded by the operator, quality of life data or symptom score data recorded by the patient, arrhythmia recurrence recorded through implanted devices (e.g. pacemakers or loop recorders), patient self-monitoring devices including but limited to mobile phones, smart watches or other wearable devices where data may include but not be limited to, accelerometer data, electrograms, heart rate monitoring, and exercise capacity.

These data, where available, will be used by the system to gauge clinical success to modify the weighting placed on the different checking algorithms and weighting criteria. This feedback on procedural and clinical outcomes to allow machine learning to improve the system is another completely novel aspect of this system.

Figure 12:
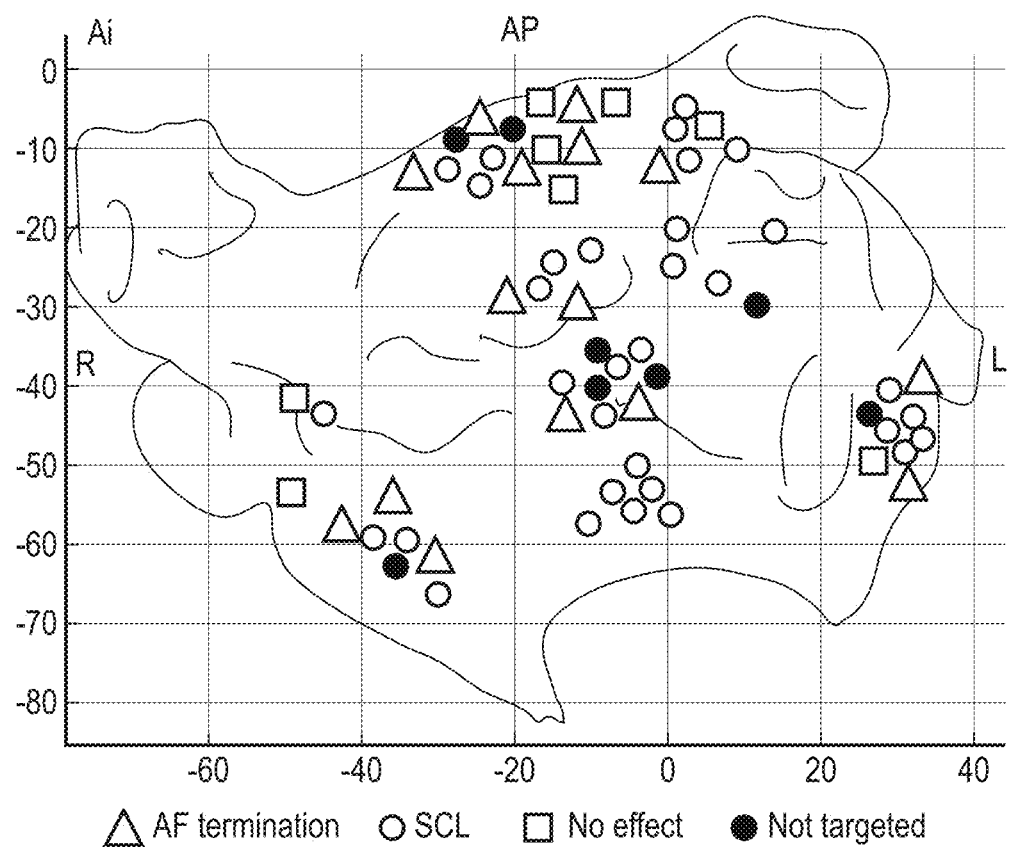
FIG. 12 shows the distribution of sites during the human clinical studies where ablation was performed and the impact of that ablation (either termination of AF, slowing of cycle length, no effect, or not targeted)
Figure 12:
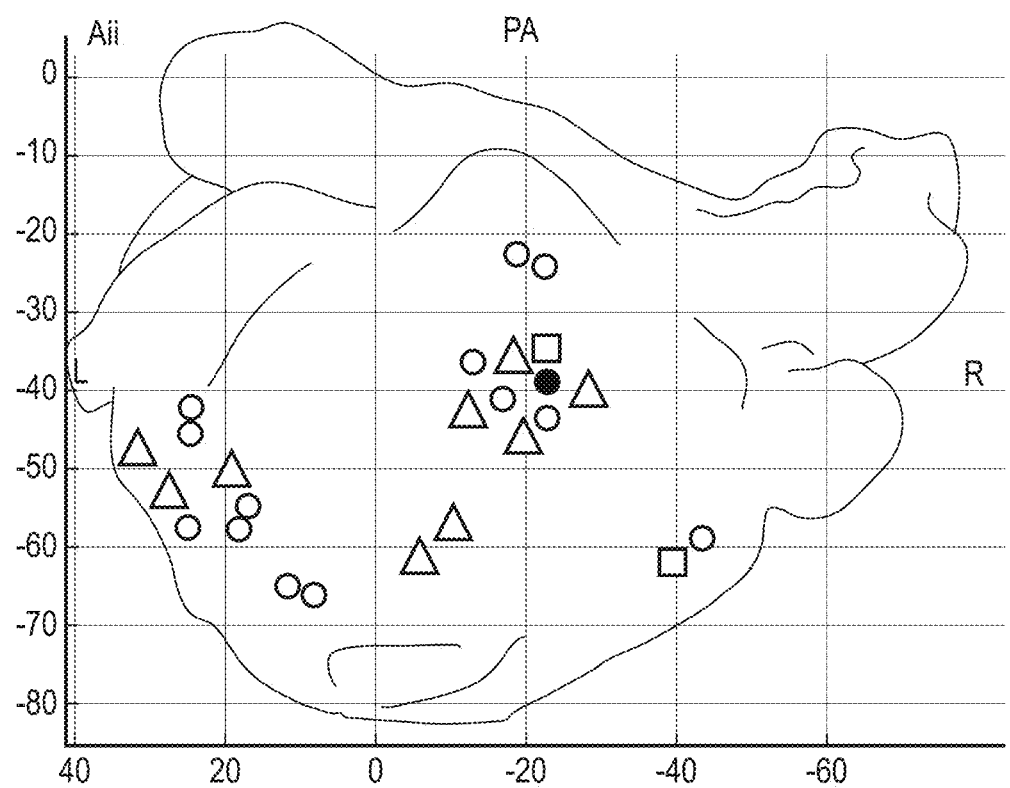
Figure 13A:
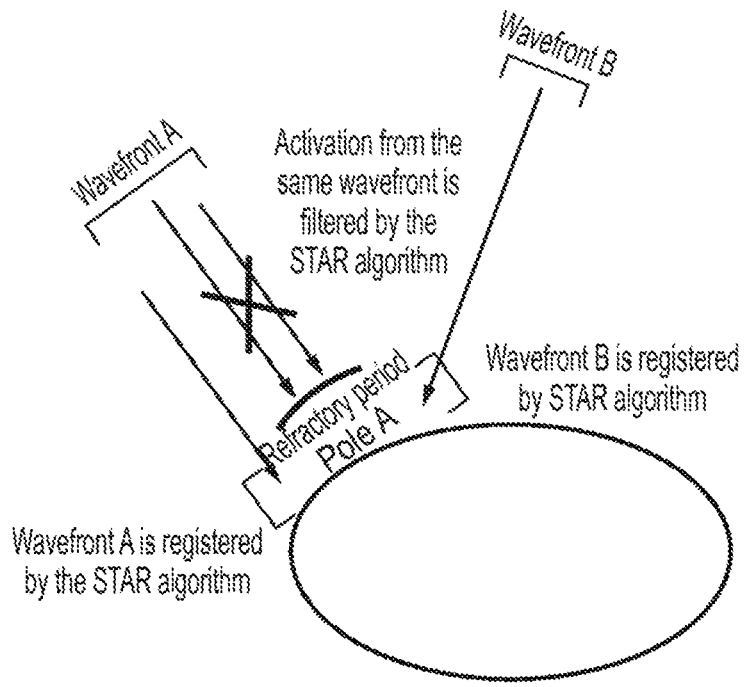
FIG. 13 A-B depict a schematic illustration of the way in which refractory periods and plausible activation time differences can be used in methods according to one or more embodiments of the present invention.
Figure 13B:
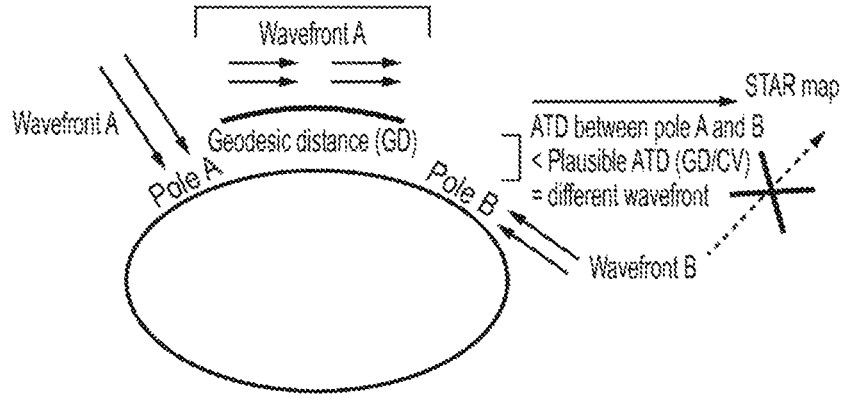

FIG. 12 is an example of the distribution of ablation sites guided by STAR mapping, locations from a series of patients are placed on an exemplary single geometry in order to indicate the general distribution of mapping sites. It is apparent that the general spatial clustering of sites at which ablation resulted in a positive effect may be used as an input modifying factor to inform weighting of future patients in a manner as described above. The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A computer implemented method to identify one or more areas of the heart muscle responsible for supporting or initiating abnormal heart rhythms using electrogram data including at least electrogram activation data recorded from a plurality of electrodes obtained from a corresponding series of sensing locations on the heart over a recording time period, the electrogram activation data including data on a plurality of activations and further including activation signals of the heart muscle, the method including the steps of:
   a) setting a pre-defined geodesic distance,
   b) dividing the recording time period into several analysis time periods, and pairing each sensing location with a plurality of other sensing locations from within the defined geodesic distance, thus forming a plurality of location pairings;
   c) for each of the analysis time periods, defining the relative timing of each activation signal for each location within each pairing,
   d) determining whether the relative timing of the activation signals falls within a defined range of plausible biological parameters,
   e) defining the leading signal of the pair for each activation within the respective analysis time period; and
   f) assigning a series of lead signal scores to each electrogram pairing acquired within each analysis time period based on the proportion of time within the respective analysis time period that each activation signal is leading within each pairing;
   g) repeating, at least once, the analysis steps b-f, each repetition being for the same sensing locations and for analysis time periods overlapping with analysis time periods of at least one other of the repetitions;
   h) combining each analysis time period for each signal location to provide a statistical measure of the proportion that each signal location tends to lead relative to other locations within a defined geodesic area; and
   i) relating lead signal scores from overlapping geodesic areas to provide relative combined lead signal scores; to provide an indication of the relative likelihood that each sensing location is generally preceding other areas and is therefore at or adjacent to a driver area of the abnormal heart rhythm.

2. The computer implemented method of claim 1, wherein lead signal scores acquired over multiple time periods are used to identify one or more activation sequences across all the electrodes recorded simultaneously over those time periods.

3. The computer implemented method of claim 1, wherein global signal scores are adjusted based on models of likely relative importance of each signal and location.

4. The computer implemented method of claim 1, wherein the predefined geodesic distance is no less than 0.2 cm and no more than 6 cm.

5. The computer implemented method of claim 1, further comprising the step of prioritising or rejecting lead signal scores based on properties of the simultaneously acquired electrograms from the plurality of locations available, the properties including one or more of:
   cycle length, activation sequence, timings after change in cycle length, and electrogram morphology.

6. The computer implemented method of claim 1, wherein the combined lead signal scores are modified depending on anatomical location, or other known modifiers acquired over the recording time period or from prior data that are associated with ablation efficacy to provide modified leading signal scores.

7. The computer implemented method of claim 6, wherein the modifiers are generated using one or more of: previous patient data; static or dynamic calculations from raw data; and a computational or statistical model.

8. The computer implemented method of claim 7 wherein the modifiers are generated using a feedback deep-learning model within a neural network.

9. The method of claim 1, further comprising generating a display output to display a graphical representation of the assigned lead signal scores, wherein the graphical representation is a 3D graphical representation with graphical representations of the lead signal scores displayed in spatial arrangement corresponding to the spatial arrangement of the corresponding sensing locations on the heart.

10. A computer system for identifying one or more areas of the heart muscle responsible for supporting or initiating abnormal heart rhythms using electrogram data including at least electrogram activation data recorded from a plurality of electrodes obtained from a corresponding series of sensing locations on the heart over a recording time period, the electrogram activation data including data on a plurality of activations and further including activation signals of the heart muscle, the system comprising:
 a processor;
 a first memory for storing received electrogram data; and
 a second memory having program code stored therein that when executed by the processor causes the system to:
  i) set pre-defined geodesic distance,
  ii) divide the recording time period into several analysis time periods, pairing each sensing location with a plurality of other sensing locations from within the defined geodesic distance, thus forming a plurality of location pairings;
  iii) for each of the analysis time periods, define the relative timing of each activation signal for each location within each pairing,
  iv) determine whether the relative timing of activation signals falls within a defined range of plausible biological parameters,
  v) define the leading signal of the pair for each electrogram activation within the respective analysis time period;
  vi) assign a series of lead signal scores to each electrogram pairing acquired within each analysis time period based on the proportion of time within the respective analysis time period that each activation signal is leading within each pairing;
  vii) repeat the execution of steps ii)-vi), each repetition being for different electrogram activation data for the same location and for analysis time periods overlapping with analysis time periods of at least one other of the repetitions;
  viii) combine each analysis time period for each signal location to provide a statistical measure of the proportion that each signal location tends to lead relative to other locations within a defined geodesic area;
  ix) relate lead signal scores from overlapping geodesic areas to provide relative combined lead signal scores; and,
  x) provide, via an output device, an indication of the relative likelihood that each sensing location is generally preceding other areas and is therefore at or adjacent to a driver area of the abnormal heart rhythm.

11. The computer system of claim 10, wherein the computer system is configured to acquire lead signal scores over multiple time periods and is further configured to identify one or more activation sequences across all the electrodes recorded simultaneously over those time periods.

12. The computer system of claim 10, wherein the computer system is configured to adjust global signal scores based on models of likely relative importance of each signal and location.

13. The computer system claim 10, wherein the pre-defined geodesic distance is no less than 0.2 cm and no more than 6 cm.

14. The computer system of claim 10, further configured to prioritise or reject lead signal scores based on properties of the simultaneously acquired electrograms from the plurality of locations available, the properties including one or more of:
 cycle length, activation sequence, timings after change in cycle length, and electrogram morphology.

15. The computer system of claim 10, wherein the computer system is configured to modify the combined lead signal scores depending on anatomical location, or other known modifiers acquired over a recording time period or from prior data that are associated with ablation efficacy to provide modified leading signal scores.

16. The computer system of claim 15, wherein modifiers are generated using one or more of: previous patient data; static or dynamic calculations from raw data; and a computational or statistical model.

17. The computer system of claim 16, further comprising a neural network having a feedback deep-learning model configured to generate the modifiers.

18. The computer system of claim 10, further configured to generate a display output to display a graphical representation of the assigned lead signal scores, wherein the graphical representation is a 3D graphical representation with graphical representations of the lead signal scores displayed in spatial arrangement corresponding to the spatial arrangement of the corresponding sensing locations on the heart.

19. A system including the computer system of claim 10, the system further comprising a multipolar electrical catheter and an interface arrangement via which signals from the catheter can be stored to the first memory, the interface arrangement comprising signal processing means including an analogue to digital converter.

20. A computer implemented method to identify one or more areas of the heart muscle responsible for supporting or initiating abnormal heart rhythms using electrogram data including at least electrogram activation data recorded from a plurality of electrodes obtained from a corresponding series of sensing locations on the heart over a recording time period, the electrogram activation data including data on a plurality of activations and further including activation signals of the heart muscle; the method including the steps of:
 a) setting a pre-defined geodesic distance,
 b) dividing the recording time period into several analysis time periods, and pairing each sensing location with a plurality of other sensing locations from within the defined geodesic distance, thus forming a plurality of location pairings;
 c) for each of the analysis time periods, defining the relative timing of each activation signal for each location within each pairing,
 d) determining whether the relative timing of the activation signals falls within a defined range of plausible biological parameters,
 e) defining the leading signal of the pair for each activation within the respective analysis time period;
 f) assigning a series of lead signal scores to each electrogram pairing acquired within each analysis time period based on the proportion of time within the respective analysis time period that each activation signal is leading within each pairing;
 g) repeating, at least once, the analysis steps b-f, each repetition being for the same sensing locations and for analysis time periods overlapping with analysis time periods of at least one other of the repetitions;
 h) combining each analysis time period for each signal location to provide a statistical measure of the proportion that each signal location tends to lead relative to other locations within a defined geodesic area;
 i) relating lead signal scores from overlapping geodesic areas to provide relative combined lead signal scores; and, j) generating a display output to display a graphical representation of the assigned lead signal scores, wherein the graphical representation is a 3D graphical representation with graphical representations of the lead signal scores displayed in spatial arrangement corresponding to the spatial arrangement of the corresponding sensing locations on the heart.

21. A computer system for identifying one or more areas of the heart muscle responsible for supporting or initiating abnormal heart rhythms using electrogram data including at least electrogram activation data recorded from a plurality of electrodes obtained from a corresponding series of sensing locations on the heart, the electrogram activation data including data on a plurality of activations and further including activation signals of the heart muscle, the system comprising:

a processor;
a first memory for storing received electrogram data; and
a multipolar electrical catheter and an interface arrangement configured to communicate signals from the catheter to the first memory, the interface arrangement comprising signal processing means including an analogue to digital converter;
a second memory having program code stored therein that when executed by the processor causes the system to:
i) set pre-defined geodesic distance,
ii) divide the recording time period into several analysis time periods, pairing each sensing location with a plurality of other sensing locations from within the defined geodesic distance, thus forming a plurality of location pairings;
iii) for each of the analysis time periods, define the relative timing of each activation signal for each location within each pairing,
iv) determine whether the relative timing of activation signals falls within a defined range of plausible biological parameters,
v) define the leading signal of the pair for each electrogram activation within the respective analysis time period;
vi) assign a series of lead signal scores to each electrogram pairing acquired within each analysis time period based on the proportion of time within the respective analysis time period that each activation signal is leading within each pairing;
vii) repeat the execution of steps ii)-vi), each repetition being for different electrogram activation data for the same location and for analysis time periods overlapping with analysis time periods of at least one other of the repetitions;
viii) combine each analysis time period for each signal location to provide a statistical measure of the proportion that each signal location tends to lead relative to other locations within a defined geodesic area;
ix) relate lead signal scores from overlapping geodesic areas to provide relative combined lead signal scores; and,
x) provide, via an output device, an indication of the relative likelihood that each sensing location is generally preceding other areas and is therefore at or adjacent to a driver area of the abnormal heart rhythm;

the computer system further comprising a neural network having a feedback deep-learning model configured to modify the combined lead signal scores depending on one or more of anatomical location and from prior data associated with ablation efficacy.

* * * * *